United States Patent
Fung et al.

(10) Patent No.: US 12,209,112 B2
(45) Date of Patent: Jan. 28, 2025

(54) METHODS OF PREVENTING OR TREATING DISEASES, CONDITIONS, OR DISORDERS ASSOCIATED WITH CHEMOTHERAPY

(71) Applicant: The Chinese University of Hong Kong, Hong Kong (CN)

(72) Inventors: Erik Yee Mun George Fung, Hong Kong (CN); Ellen Ngar-Yun Poon, Hong Kong (CN); Hangqi Luo, Zhuji (CN)

(73) Assignee: THE CHINESE UNIVERSITY OF HONG KONG, Hong Kong (CN)

(*) Notice: Subject to any disclaimer, the term of this patent is extended or adjusted under 35 U.S.C. 154(b) by 0 days.

(21) Appl. No.: 17/932,302

(22) Filed: Sep. 15, 2022

(65) Prior Publication Data
US 2024/0092850 A1 Mar. 21, 2024

(51) Int. Cl.
*C07K 14/475* (2006.01)
*A61P 43/00* (2006.01)

(52) U.S. Cl.
CPC ............ *C07K 14/475* (2013.01); *A61P 43/00* (2018.01)

(58) Field of Classification Search
None
See application file for complete search history.

(56) References Cited

U.S. PATENT DOCUMENTS

2018/0207236 A1* 7/2018 Kumar ................. C07K 14/475

OTHER PUBLICATIONS

Anonymous "Side effects Chemotherapy" https://www.nhs.uk/conditions/chemotherapy/side-effects (Year: 2023).*
Anonymous "Side Effects of Cancer Treatment" https://www.cdc.gov/cancer/survivors/patients/side-effects-of-treatment.htm (Year: 2023).*
Borner et al. "GDF15 Induces Anorexia through Nausea and Emesis" Cell Metabolism 31:351-362. (Year: 2020).*
Breen et al. "GDF-15 Neutralization Alleviates Platinum-Based Chemotherapy-Induced Emesis, Anorexia, and Weight Loss in Mice and Nonhuman Primates" Cell Metabolism 32:938-950. (Year: 2020).*
Breen et al. "Growth differentiation factor 15 (GDF-15) as a key regulator of cachexia induced by platinum-based chemotherapy" J. Clinical Oncology 38:e24162. (Year: 2020).*
Chelette et al. "The GDF15-GFRAL axis mediates chemotherapy-induced fatigue in mice" Brain Behavior and Immunity 108:45-54. (Year: 2023).*
Baek et al., Growth differentiation factor 15 (GDF15): A survival protein with therapeutic potential in metabolic diseases. Pharmacology & Therapeutics, Jun. 2019, vol. 198, pp. 46-58.
Berthiaume et al. Adriamycin-induced oxidative mitochondrial cardiotoxicity. Cell Biology and Toxicology, 2007, vol. 23, No. 1, pp. 15-25.
Cova et al. Subcellular distribution of two spin trapping agents in rat heart: possible explanation for their different protective effects against doxorubicin-induced cardiotoxicity. Free Radical Research Communications, 1992, vol. 15, No. 6, pp. 353-360.
Gianni et al. Human pharmacokinetic characterization and in vitro study of the interaction between doxorubicin and paclitaxel in patients with breast cancer. Journal of Clinical Oncology, 1997, vol. 15, No. 5, pp. 1906-1915.
Holmgren et al. Identification of novel biomarkers for doxorubicin-induced toxicity in human cardiomyocytes derived from pluripotent stem cells. Toxicology, 2015, vol. 328, pp. 102-111.
Hu et al. miR-200a Attenuated Doxorubicin-Induced Cardiotoxicity through Upregulation of Nrf2 in Mice. Oxidative Medicine and Cellular Longevity, 2019, vol. 2019, 1512326.
Kempf et al. The transforming growth factor-beta superfamily member growth-differentiation factor-15 protects the heart from ischemia/reperfusion injury. Circulation Research, 2006, vol. 98, No. 3, pp. 351-360.
Khanna et al. Increased Risk of All Cardiovascular Disease Subtypes Among Childhood Cancer Survivors. Circulation, 2019, vol. 140, No. 12, pp. 1041-1043.
Langer. Dexrazoxane for the treatment of chemotherapy-related side effects. Cancer Management and Research, 2014, vol. 6, pp. 357-363.
Li et al. Doxorubicin Blocks Cardiomyocyte Autophagic Flux by Inhibiting Lysosome Acidification. Circulation, 2016, vol. 133, No. 17, pp. 1668-1687.
Maayah et al. Resveratrol reduces cardiac NLRP3-inflammasome activation and systemic inflammation to lessen doxorubicin-induced cardiotoxicity in juvenile mice. FEBS Letters, 2021, vol. 595, No. 12, pp. 1681-1695.
Min et al. NAG-1/GDF15 accumulates in the nucleus and modulates transcriptional regulation of the Smad pathway. Oncogene, 2015, vol. 35, No. 3, pp. 377-388.
Montoro-Garcia et al. Growth differentiation factor-15, a novel biomarker related with disease severity in patients with hypertrophic cardiomyopathy. European Journal of Internal Medicine, 2011, vol. 23, No. 2, pp. 169-174.
Rochette et al. Insights Into Mechanisms of GDF15 and Receptor GFRAL: Therapeutic Targets. Trends in Endocrinology and Metabolism, 2020, vol. 31, No. 12, pp. 939-951.

(Continued)

*Primary Examiner* — Sudhakar Katakam
*Assistant Examiner* — Zachary J Miknis
(74) *Attorney, Agent, or Firm* — EAGLE IP LIMITED

(57) ABSTRACT

In certain embodiments, provided herein are compositions, kits, methods and uses that are useful for preventing or treating a subject suffering from one or more diseases, conditions or disorders associated with chemotherapy such as anthracycline treatment. In some embodiments, provided is a method of treating or preventing a disease, condition or disorder resulting from or exacerbated by chemotherapy treatment in a subject, comprising the step of: administering an effective amount of GDF15 to the subject prior to the chemotherapy. Other example embodiments are described herein. In certain embodiments, the provided novel compositions, kits, methods and uses are highly effective in reducing cardiac cytotoxicity, cheaper, and safer for use.

8 Claims, 25 Drawing Sheets

Specification includes a Sequence Listing.

(56) References Cited

OTHER PUBLICATIONS

Takemura et al. Doxorubicin-induced cardiomyopathy from the cardiotoxic mechanisms to management. Progress in Cardiovascular Diseases, 2007, vol. 49, No. 5, pp. 330-352.
Tan et al. Anthracycline-Induced Cardiomyopathy in Adults. Comprehensive Physiology, 2015, vol. 5, No. 3, pp. 1517-1540.
Van Asperen et al. Increased accumulation of doxorubicin and doxorubicinol in cardiac tissue of mice lacking mdr1a P-glycoprotein. British Journal of Cancer, 1999, vol. 79, No. 1, pp. 108-113.
Vuong et al. Novel Therapeutics for Anthracycline Induced Cardiotoxicity. Frontiers in Cardiovascular Medicine, Apr. 22, 2022, vol. 9, 863314.
Wang et al. Roles of Growth Differentiation Factor 15 in Atherosclerosis and Coronary Artery Disease. Journal of the American Heart Association, 2019, vol. 8, No. 17, e012826.
Wischhusen et al. Growth/Differentiation Factor-15 (GDF-15): From Biomarker to Novel Targetable Immune Checkpoint. Frontiers in Immunology, 2020, vol. 11, 951.
Xie et al. Major Adverse Cardiovascular Events and Mortality Prediction by Circulating GDF-15 in Patients with Type 2 Diabetes: A Systematic Review and Meta-Analysis. Biomolecules, 2022, vol. 12, No. 7, 934.
Xu et al. GDF15/MIC-1 functions as a protective and antihypertrophic factor released from the myocardium in association with SMAD protein activation. Circulation Research, 2006, vol. 98, No. 3, pp. 342-350.
Xu et al. Uncompensated mitochondrial oxidative stress underlies heart failure in an iPSC-derived model of congenital heart disease. Cell Stem Cell. 2022, vol. 29, No. 5, pp. 840-855, e7.
Zhang et al. Potent Paracrine Effects of human induced Pluripotent Stem Cell-derived Mesenchymal Stem Cells Attenuate Doxorubicin-induced Cardiomyopathy. Scientific Reports, 2015, vol. 5, 11235.
Zheng et al. Calpain-2 promotes MKP-1 expression protecting cardiomyocytes in both in vitro and in vivo mouse models of doxorubicin-induced cardiotoxicity. Archives of Toxicology, 2019, vol. 93, No. 4, 1051-1065.

\* cited by examiner

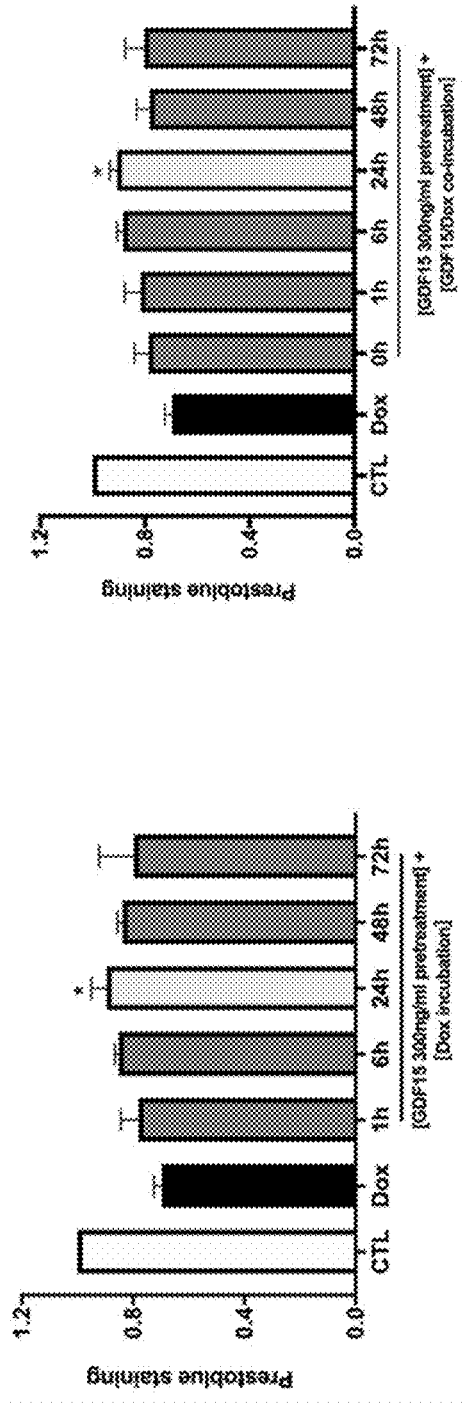
FIG. 1D
FIG. 1E
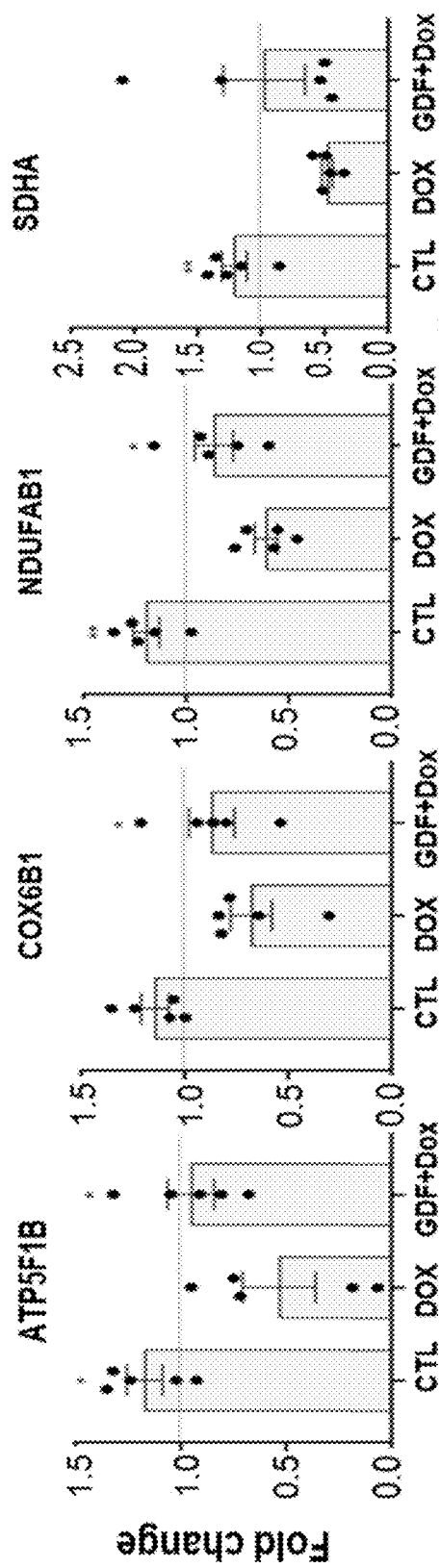
FIG. 1F

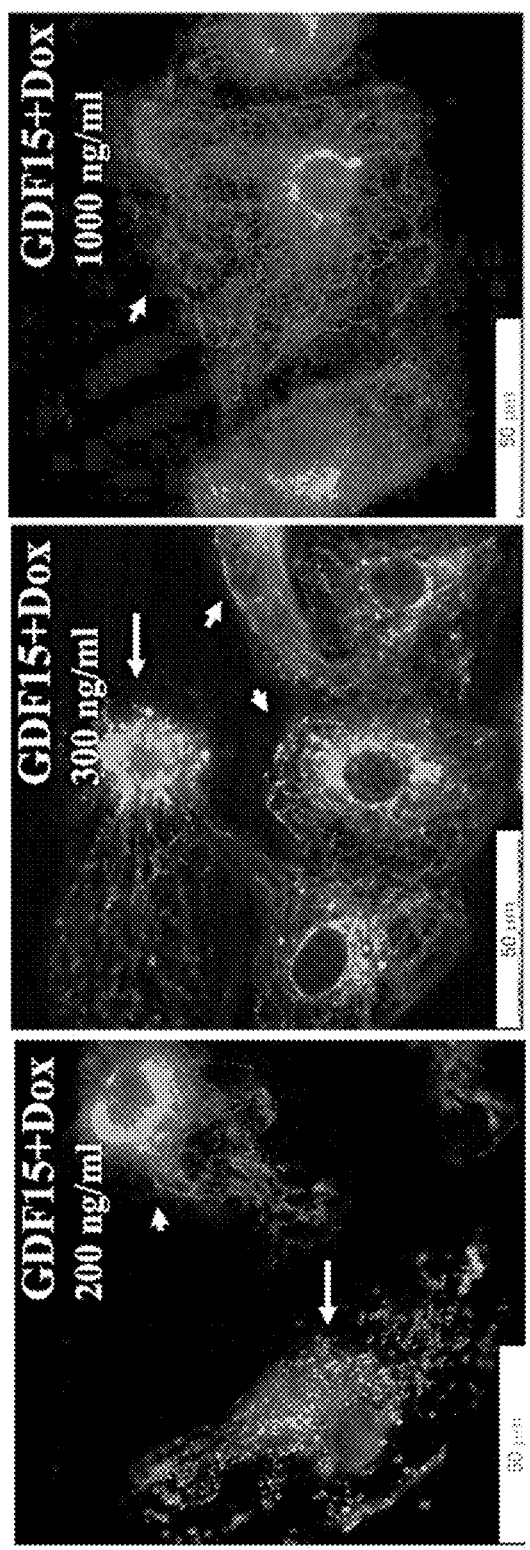

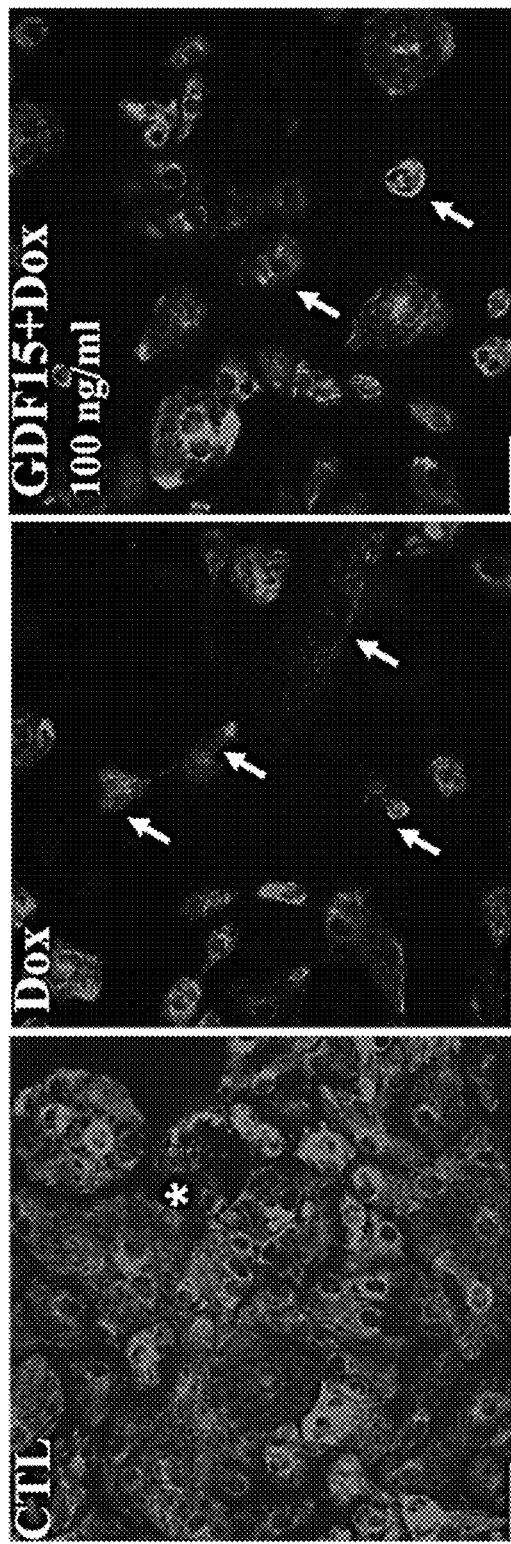

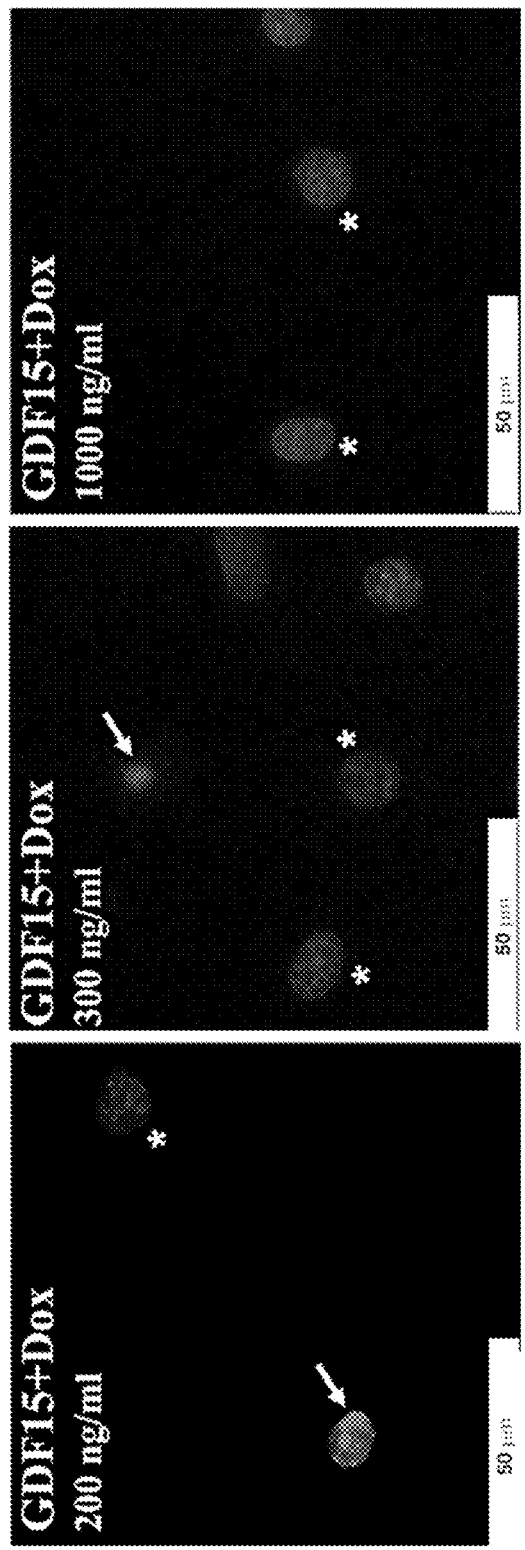

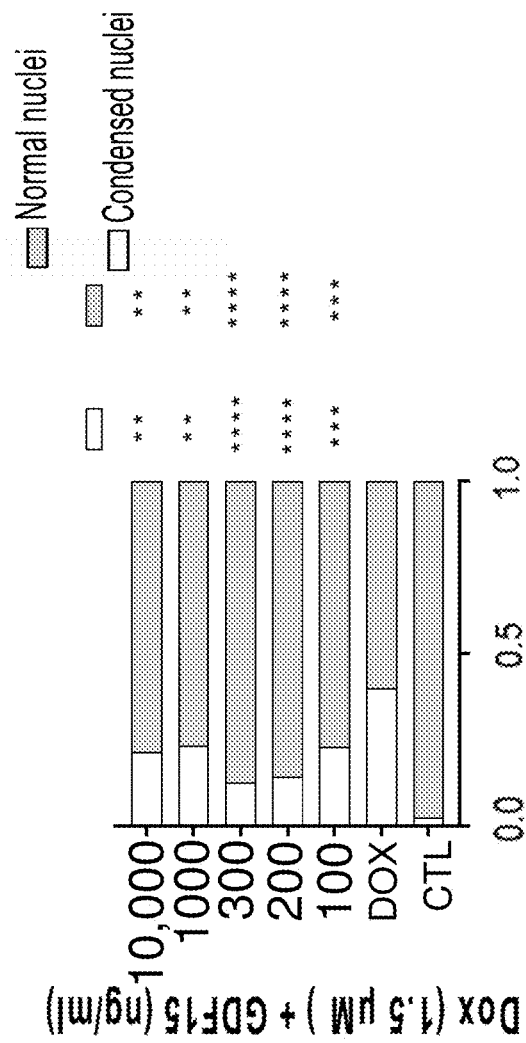
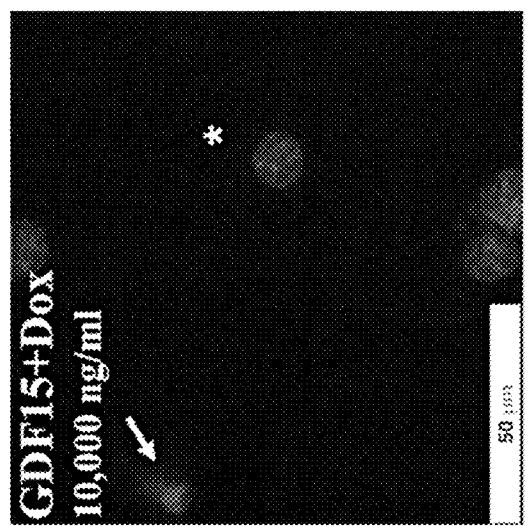
FIG. 4H
FIG. 4G

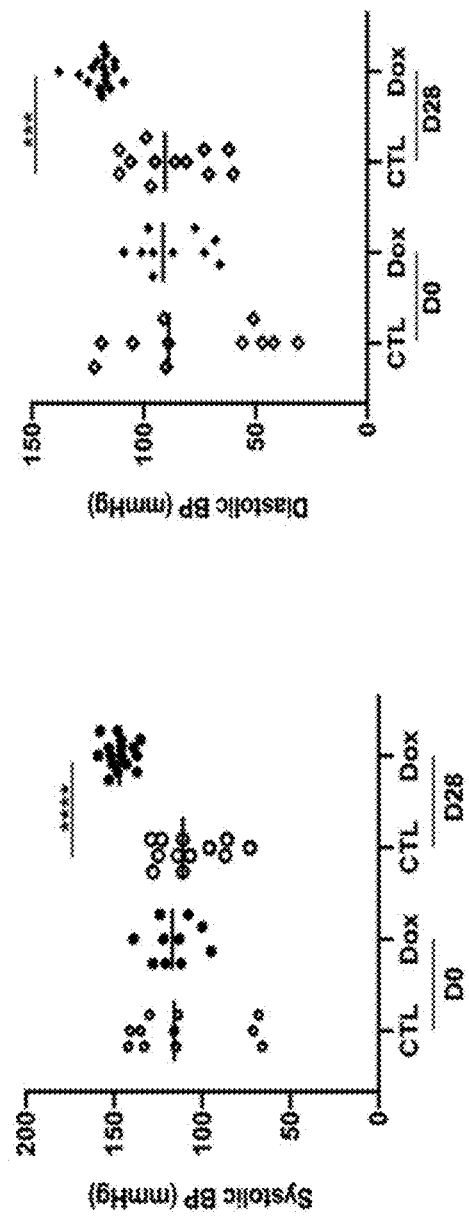
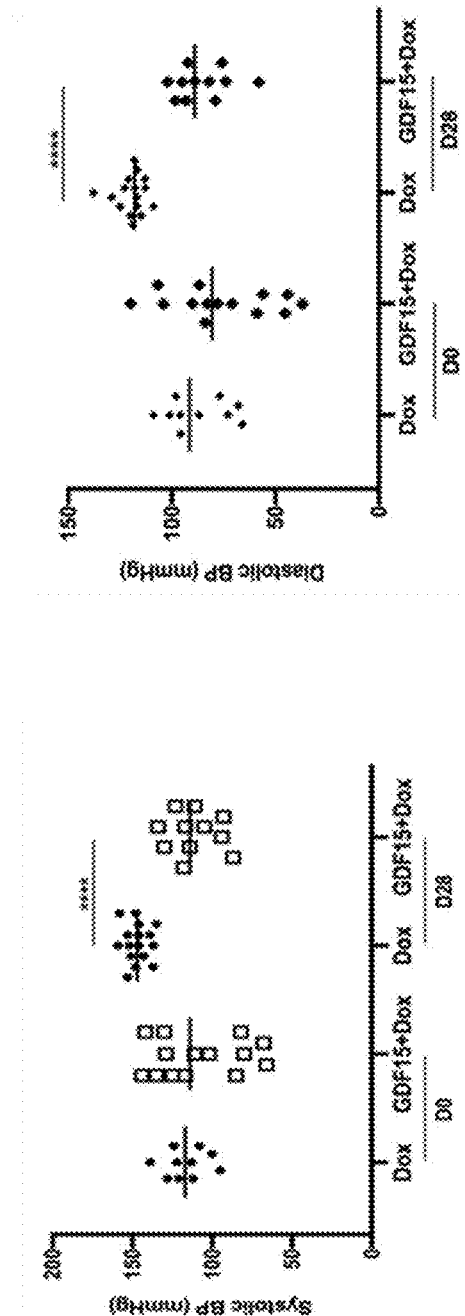
FIG. 6A
FIG. 6B
FIG. 6C
FIG. 6D

SEQUENCE LISTING

```
Sequence total quantity: 9
SEQ ID NO: 1              moltype = AA   length = 112
FEATURE                   Location/Qualifiers
source                    1..112
                          mol_type = protein
                          organism = Homo sapiens
SEQUENCE: 1
ARNGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 2              moltype = DNA   length = 20
FEATURE                   Location/Qualifiers
source                    1..20
                          mol_type = other DNA
                          organism = synthetic construct
SEQUENCE: 2
ctggtgttgg tgagaggacc                                                20

SEQ ID NO: 3              moltype = DNA   length = 20
FEATURE                   Location/Qualifiers
source                    1..20
                          mol_type = other DNA
                          organism = synthetic construct
SEQUENCE: 3
cagacacctc tgaaccagcc                                                20

SEQ ID NO: 4              moltype = DNA   length = 20
FEATURE                   Location/Qualifiers
source                    1..20
                          mol_type = other DNA
                          organism = synthetic construct
SEQUENCE: 4
cggggtgcct ttaggattca                                                20

SEQ ID NO: 5              moltype = DNA   length = 20
FEATURE                   Location/Qualifiers
source                    1..20
                          mol_type = other DNA
                          organism = synthetic construct
SEQUENCE: 5
ttctgacagc ggtggaagtc                                                20

SEQ ID NO: 6              moltype = DNA   length = 18
FEATURE                   Location/Qualifiers
source                    1..18
                          mol_type = other DNA
                          organism = synthetic construct
SEQUENCE: 6
cgcgcaggtt cctggtag                                                  18

SEQ ID NO: 7              moltype = DNA   length = 20
FEATURE                   Location/Qualifiers
source                    1..20
                          mol_type = other DNA
                          organism = synthetic construct
SEQUENCE: 7
gtcctggatg ccctctaacg                                                20

SEQ ID NO: 8              moltype = DNA   length = 20
FEATURE                   Location/Qualifiers
source                    1..20
                          mol_type = other DNA
                          organism = synthetic construct
SEQUENCE: 8
ttgcagcaca gggaggaatc                                                20

SEQ ID NO: 9              moltype = DNA   length = 20
FEATURE                   Location/Qualifiers
source                    1..20
                          mol_type = other DNA
                          organism = synthetic construct
SEQUENCE: 9
ccgtcatgta gtggatggca                                                20
```

METHODS OF PREVENTING OR TREATING DISEASES, CONDITIONS, OR DISORDERS ASSOCIATED WITH CHEMOTHERAPY

REFERENCE TO SEQUENCE LISTING

This application contains a sequence listing which has been submitted electronically in ST.26 (xml) format and is hereby incorporated by reference in its entirety. Said ST.26 copy, created on Aug. 9, 2022, is named "C064002NPRUS.xml" and is 8.73 kilobytes in size.

FIELD OF INVENTION

This application relates to compositions, kits, methods and uses that are useful for preventing or treating cancers, or useful for preventing or treating complication(s) of cancer treatments. In particular, this application relates to compositions, kits, methods and uses that are useful for preventing or treating a subject suffering from one or more diseases, conditions or disorders associated with anthracycline treatment.

BACKGROUND OF INVENTION

Anthracycline is a class of anticancer drugs that is used in a wide range of malignancies. Anthracyclines are highly effective but also dose-dependently damaging to cardiac cells and the heart (cardiotoxicity). Patients exposed to anthracyclines can develop cardiotoxicity and manifest early after exposure or present with cardiomyopathy and heart failure months to years later.

Doxorubicin is a member of the anthracycline class of cytotoxic chemotherapy. It comprises a tetracyclic ring with two quinone-hydroquinones and daunosamine structures that allow the amphipathic molecule to bind easily to cell membranes. After entering the cell and its nucleus, it binds DNA with high affinity and interferes with transcription and DNA replication.

Thousands of patients worldwide undergo anthracycline (e.g. doxorubicin, epirubicin, daunorubicin, idarubicin) chemotherapy each year, and a significant portion of them develop cardiotoxicity, cardiomyopathy, heart failure, and/or other associated harmful complications. Over half of pediatric cancer patients receive anthracycline. The risk for developing heart failure (HF) is higher in cancer survivors exposed to >250 mg/m2 doxorubicin (vs. non-exposed), with a hazard ratio of 8.6. Symptomatic HF develops in at least 2-5% of adult cancer patients treated with anthracycline. One-third of patients treated with anthracycline do not recover their baseline left ventricular ejection fraction (LVEF). Cardiotoxicity and cardiomyopathy are not simply a consequence of anthracycline dose accumulation, but can occur at any point during and subsequent to treatment. Transient decreases in ventricular systolic function are not benign.

Up to one-third of cancer patients are treated with an anticancer chemotherapeutic regimen that includes an anthracycline, of which doxorubicin (Adriamycin, among other trade names) has been the most widely used. The global doxorubicin market is estimated at USD $3.6 billion by 2027.

Available preventative options for doxorubicin cardiotoxicity are limited. Dexrazoxane (trade names: Cardioxane®, Totect® and Zinecard®) is the only U.S. Food and Drug Administration (FDA)-approved prophylaxis or pretreatment against anthracycline cardiotoxicity. However, dexrazoxane compromises anticancer efficacy of anthracycline (such as doxorubicin), causes secondary hematological malignancy including acute myeloid leukemia, and is indicated for women with, for example, metastatic breast cancer who have received a cumulative doxorubicin dose of >300 mg/m$^2$. It is highly desired to provide alternative compositions, kits, methods and uses of preventing or treating a subject suffering from one or more diseases, conditions or disorders associated with anthracycline treatment.

SUMMARY OF INVENTION

In certain embodiments, disclosed herein are novel compositions, kits, methods and uses that are useful for the prevention or treatment of cancers, and/or one or more diseases, conditions or disorders resulting from a chemotherapy treatment (for example, anthracycline such as doxorubicin). In certain embodiments, disclosed herein are methods of preventing or treating cancer and anthracycline toxicity. In certain embodiments, disclosed herein are uses of a pharmaceutical composition comprising GDF15, or a functional variant or homolog thereof in preventing or treating one or more diseases, conditions or disorders resulting from a chemotherapy treatment (for example, anthracycline such as doxorubicin).

In some embodiments, provided is a method of treating or preventing a disease, condition or disorder resulting from or exacerbated by chemotherapy treatment in a subject. In some embodiments, the method includes the step of: administering an effective amount of GDF15 to the subject receiving the chemotherapy treatment such that the disease, condition or disorder is improved.

In some embodiments, provided is a method of treating or preventing cancer in a subject, comprising the steps of:
 (a) administering a first composition comprising Growth Differentiation Factor 15 (GDF15), or a functional variant or homolog thereof, to the subject; and
 (b) administering a second composition comprising anthracycline to the subject.

In some embodiments, provided is a method of treating or preventing a disease, condition or disorder requiring anthracycline treatment in a subject in need thereof, comprising the step of administering an effective amount of GDF15 to the subject receiving the anthracycline treatment.

In some embodiments, provided is a kit for treating preventing or treating a subject suffering from cancer, comprising: a first composition comprising anthracycline; and a second composition comprising GDF15.

In some embodiments, the provided novel compositions, kits, methods and uses prevent, treat, and/or alleviate anthracycline-induced cardiotoxicity. In some embodiments, the provided novel compositions, kits, methods and uses prevent, treat, and/or alleviate damage caused by reactive oxygen species and DNA intercalation. In some embodiments, the provided novel compositions, kits, methods and uses prevent, treat, and/or alleviate cardiomyocyte apoptosis and/or inhibit expression of cardiomyocyte-specific genes for contractile proteins. In some embodiments, the provided novel compositions, kits, methods and uses prevent, treat, and/or alleviate damage or dysfunction of the mitochondria.

Advantages

There are many advantages of the compositions, kits, methods and uses of the present disclosure. In certain embodiments, provided novel compositions, kits, methods and uses have outstanding and superior performance in prevention or treatment of cancers, and/or one or more diseases, conditions or disorders resulting from a chemotherapy treatment. In certain embodiments, provided novel compositions, kits, methods and uses have outstanding and superior performance in prevention or treatment of one or more diseases, conditions or disorders resulting from anthracycline, such as doxorubicin. In certain embodiments, provided novel compositions, kits, methods and uses are highly efficacious in prevention or treatment of one or more diseases, conditions or disorders resulting from anthracycline, cheaper, and safer for use. In certain embodiments, provided novel compositions, kits, methods and uses do not compromise anticancer efficacy, nor evoke secondary hematological malignancy such as acute myeloid leukemia. In certain embodiments, viability of human cardiac cells exposed to anthracycline (such as doxorubicin) is significantly increased by the provided novel compositions, kits, methods and uses. In certain embodiments, mitochondrial dysfunction and damage from anthracycline (such as doxorubicin) are significantly attenuated by the provided novel compositions, kits, methods and uses. In certain embodiments, cardiomyocyte apoptosis following exposure to anthracycline (such as doxorubicin) is significantly reduced by the provided novel compositions, kits, methods and uses. In certain embodiments, provided novel compositions, kits, methods and uses have similar, comparable or even better efficacy to dexrazoxane in reducing cardiac cytotoxicity and cardiomyopathy. In certain embodiments, hypertension and vascular dysfunction secondary to anthracycline cardiotoxicity and nephrotoxicity are reduced by the provided novel compositions, kits, methods and uses. In certain embodiments, myocardial tissue loss, cardiomyocyte death and apoptosis in response to anthracycline is attenuated by the provided novel compositions, kits, methods and uses. In certain embodiments, cardiac fibrosis in response to anthracycline is attenuated by the provided novel compositions, kits, methods and uses.

In certain embodiments, provided novel compositions, kits, methods and uses can protect human cardiomyocytes in vitro, can protect mouse heart in vivo, can reduce mitochondrial damage, cell apoptosis and disruption of sarcomere induced by anthracycline (e.g. doxorubicin), can markedly reduce cardiac fibrosis, and can prevent hypertensive response to anthracycline (e.g. doxorubicin). In certain embodiments, provided novel compositions, kits, methods and uses demonstrate the prophylactic and therapeutic potential of exogenous recombinant human GDF15 against doxorubicin in cultured, beating human embryonic stem cell-derived cardiomyocytes (hESC-CM) in vitro, and in a mouse model of doxorubicin cardiotoxicity and cardiomyopathy in vivo. The high level of consistency in optimal dose finding, sequence and timing of GDF15 administration, and histopathological analyses from both preclinical experimental models support the use of GDF15 as a novel prophylactic and/or therapeutic agent in anthracycline cardiotoxicity and cardiomyopathy.

In certain embodiments, provided novel compositions, kits, methods and uses attenuate cardiac hypertrophy, adverse remodeling, reduce the adverse cardiac remodeling in hypertension, hypertrophic cardiomyopathy, and experimental pressure overload, and also counter cardiovascular damage induced by ischemia-reperfusion injury.

In certain embodiments, the present invention provides an alternative option to dexrazoxane in preventing or treating anthracycline-associated diseases, conditions or disorders.

BRIEF DESCRIPTION OF FIGURES

FIG. 1D is a time-response analysis of viability of hESC-CMs pretreated with GDF15 before applying doxorubicin (Dox) for the indicated times (1 h, 6 h, 24 h, 48 h, and 72 h) preceding Dox only treatment for 24 h, according to an example embodiment.

FIG. 1E is a time-response analysis of viability of hESC-CMs pretreated with GDF15 for the indicated times (1 h, 6 h, 24 h, 48 h, and 72 h) preceding coincubation with both Dox for 24 h and GDF15, according to an example embodiment.

FIG. 1F is the results of real-time PCR quantification of genes important for mitochondrial function, according to an example embodiment.

FIGS. 2A-2G are the microscopic images of mitochondrial staining using the MTDR dye to quantify and compare the proportion of hESC-CMs exposed to Dox with elongated (asterisk), punctate (arrowhead), and perinuclear (arrow) mitochondria upon pretreatment with increasing concentrations of human recombinant GDF15, according to an example embodiment.

FIGS. 3A-3G are the microscopic images of staining with the potentiometric dye, TMRE (red), to assess mitochondrial membrane potential and function in hESC-CMs exposed to Dox upon pretreatment with increasing concentrations of human recombinant GDF15, according to an example embodiment.

FIGS. 4A-4G are the microscopic images of staining with the Hoechst 33342 dye to assess nuclear condensation and morphology, and signs of apoptosis in hESC-CMs exposed to doxorubicin upon pretreatment with increasing concentrations of human recombinant GDF15, according to an example embodiment.

FIG. 4H is a graphical illustration of the proportion of normal and condensed nuclei in hESC-CMs exposed to doxorubicin upon pretreatment with increasing concentrations of human recombinant GDF15, according to an example embodiment.

FIGS. 6A-6F are the blood pressure measurements in mice upon pretreatment of GDF15 or Dex, in the presence of Dox, according to an example embodiment.

DETAILED DESCRIPTION

Figure 1C:
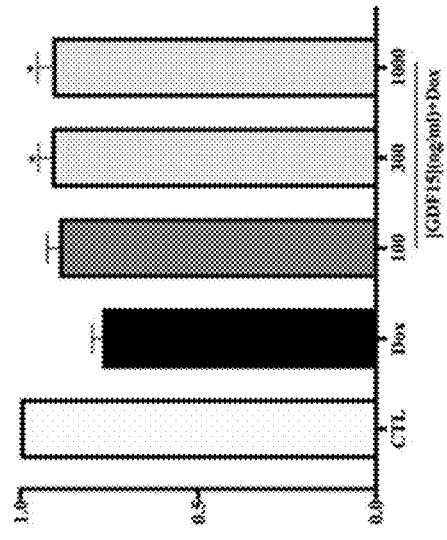
FIG. 1C is the refinement of dose findings of pretreatment with GDF15 at concentrations at 100 ng/ml, 300 ng/ml, and 1,000 ng/ml before applying doxorubicin, according to an example embodiment.

As used herein and in the claims, the terms "comprising" (or any related form such as "comprise" and "comprises"), "including" (or any related forms such as "include" or "includes"), "containing" (or any related forms such as "contain" or "contains"), means including the following elements but not excluding others. It shall be understood that for every embodiment in which the term "comprising" (or any related form such as "comprise" and "comprises"), "including" (or any related forms such as "include" or "includes"), or "containing" (or any related forms such as "contain" or "contains") is used, this disclosure/application also includes alternate embodiments where the term "comprising", "including," or "containing," is replaced with "consisting essentially of" or "consisting of". These alternate embodiments that use "consisting of" or "consisting essentially of" are understood to be narrower embodiments of the "comprising", "including," or "containing," embodiments.

For example, alternate embodiments of "a composition comprising A, B, and C" would be "a composition consisting of A, B, and C" and "a composition consisting essentially of A, B, and C." Even if the latter two embodiments are not explicitly written out, this disclosure/application includes those embodiments. Furthermore, it shall be understood that the scopes of the three embodiments listed above are different. For the sake of clarity, "comprising", including, and "containing", and any related forms are open-ended terms which allows for additional elements or features beyond the named essential elements, whereas "consisting of" is a closed end term that is limited to the elements recited in the claim and excludes any element, step, or ingredient not specified in the claim.

For the sake of clarity, "characterized by" or "characterized in" (together with their related forms as described above), does not limit or change the nature of whether the list of terms following it are open or closed. For example, in a claim directed towards "a composition comprising A, B, C, and characterized in D, E, and F", the elements D, E, and F are still open-ended terms and the claim is meant to include other elements due to the use of the word "comprising" earlier in the claim.

"Consisting essentially of" limits the scope of a claim to the specified materials, components, or steps ("essential elements") that do not materially affect the essential characteristic(s) of the claimed invention. In some embodiments, the essential characteristics are the basic and novel characteristic(s) of the claimed invention. For example, in some embodiments, the essential elements of a composition of the disclosure can be "Xmg to Ymg" of compound A. Even if the composition includes additional excipients, as long as the additional excipients do not materially affect the essential characteristics of the compound, e.g., in compound A's ability to bind to XX target or to treat YY disease, then such embodiment that "consists essentially of compound A" still includes compositions with the aforementioned additional excipients.

As used herein, the singular forms "a", "an" and "the" are intended to include the plural forms as well, unless the context clearly indicates otherwise. Where a range is referred in the specification, the range is understood to include each discrete point within the range. For example, 1-7 means 1, 2, 3, 4, 5, 6, and 7.

As used herein, the term "about" is understood as within a range of normal tolerance in the art and not more than ±10% of a stated value. By way of example only, about 50 means from 45 to 55 including all values in between. As used herein, the phrase "about" a specific value also includes the specific value, for example, about 50 includes 50.

As used herein and in the claims, an "effective amount", is an amount that is effective to achieve at least a measurable amount of a desired effect. For example, the amount may be effective to elicit an immune response, and/or it may be effective to elicit a protective response, against a pathogen bearing the polypeptide of interest. In some embodiments, the amount may be effective to elicit an immune response against cancer or tumor.

As used herein and in the claims, a "subject" refers to animals such as mammals, including, but not limited to, primates (e.g. humans), cows, sheep, goats, horses, dogs, cats, rabbits, rats, mice and the like. In certain embodiments, the subject refers to human.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "prevent", "preventing", "preventive", "preventative" or "prevention" refers the methods of reducing the risk of the onset, relapse or spread of a disease or disorder or one or more of their symptoms.

As used herein, the term "functional variant or homolog" refers to a functional variant or a function homolog, respectively. The term "functional variant" refers to a variant polypeptide that differs from the wild-type polypeptide in chemical structure and retains substantially or the same function. "Functional homolog" refers to a nucleotide sequence that has a sequence that differs from the original nucleotide sequence but still encodes the same amino acid sequence due to the use of degenerated genetic code.

As used herein, the terms "growth differentiation factor 15", "Growth Differentiation Factor 15", "GDF-15" or "GDF15" (also known as macrophage inhibitory cytokine 1 (MIC-1), nonsteroidal anti-inflammatory drug-activated gene-1 (NAG-1), prostate-derived factor (PDF), placental transforming growth factor-beta (pTGFB), placental bone morphogenetic protein (PLAB), etc.) are used interchangeably to refer to a protein classified as a member of the transforming growth factor-beta superfamily that uses SMAD and other associated intracellular proteins for signal transduction and downstream gene transcription. "Growth differentiation factor 15" or "GDF15" also include, but are not limited to, the functional variant or homolog thereof.

As used herein, the terms "recombinant human growth differentiation factor 15", "human recombinant GDF15", "recombinant human GDF15" or "rhGDF15" are used interchangeably to refer to a human growth differentiation factor 15 protein prepared via genetic engineering, and also include, but are not limited to, the functional variant or homolog thereof.

As used herein, the term "cancer" refers to a proliferative disorder caused or characterized by the proliferation of cells which have lost susceptibility to normal growth control. A "cancer" may include tumors and any other proliferative disorders. Cancers of the same tissue type usually originate in the same tissue, and may be divided into different subtypes based on their biological characteristics. Examples include but not limited to leukemias, lymphomas, breast, stomach, uterine, ovarian, bladder cancer, and lung cancers.

As used herein, the terms "chemotherapy" or "chemotherapeutic" refer to a chemical treatment intended to be therapeutic with respect to a disease, condition or disorder. A "chemotherapy" or "chemotherapeutic" is commonly intended to kill or halt the replication and/or spread of cells in a patient that grow and divide quickly, including, but not limited to cancer cells.

As used herein, the term "anthracycline" refers to a group of antibiotics having the basic structure of a tetracyclic molecule with an anthraquinone backbone connected to a sugar moiety by a glycosidic linkage. Examples of anthracycline include, but are not limited to doxorubicin, epirubicin, daunorubicin, and idarubicin. "Anthracycline" also includes, but are not limited to, the derivative, analog or salt thereof. "Anthracycline treatment" refers to one or multiple treatment regimes of one or multiple rounds (or cycles) of anthracycline administration(s), either alone or in combination with other therapeutics.

As used herein, the terms "doxorubicin", "Doxorubicin" or "Dox" are used interchangeably to refer to a member of anthracycline family comprising a structure of tetracyclic ring with two quinone-hydroquinones and daunosamine structures. "Doxorubicin" or "Dox" also include, but are not limited to, the derivative, analog or salt thereof.

As used herein, the terms "dexrazoxane", "Dexrazoxane" or "Dex" (Trade names: Cardioxane®, Totect® and Zinecard®) are used interchangeably to refer to a bisdioxopiperazine drug with iron-chelating, chemoprotective, cardioprotective, and antineoplastic activities. "Dexrazoxane" or "Dex" also include, but are not limited to, the derivative, analog or salt thereof.

As used herein, the term "cardiotoxicity" refers to an occurrence of heart electrophysiology dysfunction or muscle damage that results in heart toxicity. In certain embodiments, the term cardiotoxicity includes cardiac cytotoxicity which refers to cytotoxicity to cardiac cells or cardiomyocytes.

As used herein, the term "anthracycline cardiotoxicity" refers to an occurrence of heart electrophysiology dysfunction or heart muscle damage associated with or induced by anthracycline.

Although the description referred to particular embodiments, the disclosure should not be construed as limited to the embodiments set forth herein.

NUMBERED EMBODIMENTS

Embodiment 1: A method of treating or preventing a disease, condition or disorder resulting from or exacerbated by chemotherapy treatment in a subject, comprising the step of:
administering an effective amount of GDF15 to the subject receiving the chemotherapy treatment such that the disease, condition or disorder is improved.
Embodiment 2: The method of embodiment 1, wherein the step of administering an effective amount of GDF15 to the subject is performed prior to the chemotherapy treatment.
Embodiment 3: The method of embodiment 1, wherein the chemotherapy treatment comprises at least one round of anthracycline administration, and wherein the step of administering the effective amount of GDF15 to the subject is performed prior to each round of anthracycline administration.
Embodiment 4: The method of any one of the preceding embodiments, wherein the anthracycline is selected from the group consisting of doxorubicin, epirubicin, daunorubicin, and idarubicin.
Embodiment 5: The method of any one of the preceding embodiments, wherein the GDF15 is or comprises a recombinant human GDF15.
Embodiment 6: The method of any one of the preceding embodiments, wherein the GDF15 comprises an amino acid sequence SEQ ID NO:1, or a functional variant or homolog thereof.
Embodiment 7: The method of any one of the preceding embodiments, wherein the disease, condition or disorder is selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death.
Embodiment 8: A method of treating or preventing cancer in a subject, comprising the steps of:
(a) administering at least one round of a first composition comprising Growth Differentiation Factor 15 (GDF15), or a functional variant or homolog thereof, to the subject; and (b) administering at least one round of a second composition comprising anthracycline to the subject.

Embodiment 9: The method of embodiment 8, wherein step (a) is performed prior to step (b).

Embodiment 10: The method of embodiment 8, wherein step (b) comprises a plurality of rounds of anthracycline administration.

Embodiment 11: The method of embodiment 9, wherein steps (a) and (b) together are performed more than one time.

Embodiment 12: The method of any one of the embodiments 8-10, wherein the anthracycline is selected from the group consisting of doxorubicin, epirubicin, daunorubicin, and idarubicin.

Embodiment 13: The method of any one of the embodiments 8-11, wherein the GDF15 or functional variant or homolog thereof is a recombinant human GDF15.

Embodiment 14: The method of any one of the embodiments 8-12, wherein the GDF15 comprises an amino acid sequence of SEQ ID NO:1, or a functional variant or homolog thereof.

Embodiment 15: A method of treating or preventing a disease, condition or disorder requiring anthracycline treatment in a subject in need thereof, comprising the step of administering an effective amount of GDF15 to the subject receiving the anthracycline treatment.

Embodiment 16: The method of embodiment 15, wherein the effective amount of GDF15 is administered prior to the anthracycline treatment.

Embodiment 17: The method of embodiment 15, wherein the anthracycline treatment comprises at least one round of anthracycline administration, and wherein the step of administering the effective amount of GDF15 to the subject is performed prior to each round of anthracycline administration.

Embodiment 18: The method of any one of the embodiments 15-17, wherein the anthracycline is selected from the group consisting of doxorubicin, epirubicin, daunorubicin, and idarubicin.

Embodiment 19: The method of any one of the embodiments 15-18, wherein the GDF15 comprises an amino acid sequence of SEQ ID NO:1, or a functional variant or homolog thereof.

Embodiment 20: A kit for treating preventing or treating a subject suffering from cancer, comprising:
a first composition comprising anthracycline; and
a second composition comprising GDF15.

Embodiment 21: The kit of embodiment 20, wherein the anthracycline is selected from the group consisting of doxorubicin, epirubicin, daunorubicin, and idarubicin.

Embodiment 22: The kit of embodiments 20 or 21, wherein the GDF15 comprises an amino acid sequence of SEQ ID NO:1, or a functional variant or homolog thereof.

Embodiment 23: A use of a pharmaceutical composition comprising GDF15, or a functional variant or homolog thereof, for preventing or treating one or more diseases, conditions or disorders resulting from a chemotherapy treatment.

Embodiment 24: The use of embodiment 23, wherein the chemotherapy treatment comprises administering anthracycline.

Embodiment 25: The use of embodiment 24, wherein the anthracycline is selected from the group consisting of doxorubicin, epirubicin, daunorubicin, and idarubicin.

Embodiment 26: The use of embodiment 25, wherein the anthracycline is doxorubicin.

Embodiment 27: The use of any one of the embodiments 23-26, wherein the GDF15 is a recombinant human GDF15.

Embodiment 28: The use of any one of the embodiments 23-27, wherein the GDF15 comprises an amino acid sequence SEQ ID NO:1.

Embodiment 29: The use of any one of the embodiments 23-28, wherein the diseases, conditions or disorders are selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death.

Embodiment 30: A use of a composition for preventing or treating anthracycline-associated cardiotoxicity, cardiomyopathy and/or heart failure, wherein the composition comprises GDF15, or a functional variant or homolog thereof.

Embodiment 31: The use of embodiment 30, wherein the anthracycline is selected from the group consisting of doxorubicin, epirubicin, daunorubicin, and idarubicin.

Embodiment 32: The use of embodiment 31, wherein the anthracycline is doxorubicin.

Embodiment 33: The use of any one of the embodiments 30-32, wherein the GDF15 is a recombinant human GDF15.

Embodiment 34: The use of any one of the embodiments 30-33, wherein the GDF15 comprises an amino acid sequence SEQ ID NO:1, or a functional variant or homolog thereof.

Embodiment 35: A use of a composition in the manufacture of a medicament for preventing or treating one or more diseases, conditions or disorders resulting from chemotherapy treatment, wherein the composition comprises GDF15, or a functional variant or homolog thereof.

Embodiment 36: The use of embodiment 35, wherein the chemotherapy treatment comprises anthracycline.

Embodiment 37: The use of embodiment 36, wherein the anthracycline is selected from the group consisting of doxorubicin, epirubicin, daunorubicin, and idarubicin.

Embodiment 38: The use of embodiment 37, wherein the anthracycline is doxorubicin.

Embodiment 39: The use of any one of the embodiments 35-38, wherein the GDF15 is a recombinant human GDF15.

Embodiment 40: The use of any one of the embodiments 35-39, wherein the GDF15 comprises an amino acid sequence SEQ ID NO:1.

Embodiment 41: The use of any one of the embodiments 35-40, wherein the diseases, conditions or disorders resulting from chemotherapy treatment are selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death.

Embodiment 42: A method of increasing viability of a cardiac cell subject to anthracycline exposure comprising the step of contacting the cardiac cell with GDF15 or a functional variant or homolog thereof prior to the anthracycline exposure.

Embodiment 43: A method of reducing mitochondrial dysfunction or damage caused by anthracycline exposure in a cardiac cell comprising the step of contacting the cardiac cell with GDF15 or a functional variant or homolog thereof prior to the anthracycline exposure.

Embodiment 44: The method of embodiment 43, wherein the mitochondrial dysfunction or damage causes cardiomyocyte apoptosis.

Embodiment 45: A unit dosage form or a composition for treating or preventing a disease, condition, or disorder resulting from or exacerbated by chemotherapy treatment in a subject, comprising recombinant human GDF15 and a pharmaceutically acceptable salt or carrier thereof.

EXAMPLES

Provided herein are examples that describe in more detail certain embodiments of the present disclosure. The example provided herein are merely for illustrative purposes and are not meant to limit the scope of the invention in any way. All references given below and elsewhere in the present application are hereby included by reference. In one aspect, provided is a method of treating or preventing a disease, condition or disorder resulting from or exacerbated by chemotherapy treatment in a subject, comprising the step of: administering an effective amount of GDF15 to the subject receiving the chemotherapy treatment such that the disease, condition or disorder is improved.

In some embodiments, the step of administering an effective amount of GDF15 to the subject is performed prior to the chemotherapy treatment.

In some embodiments, the chemotherapy treatment comprises at least one round of anthracycline administration, and wherein the step of administering the effective amount of GDF15 to the subject is performed prior to each round of anthracycline administration.

In some embodiments, the chemotherapy treatment comprises a plurality of rounds of anthracycline administrations, and wherein the step of administering the effective amount of GDF15 to the subject is performed prior to each round of anthracycline administration.

In some embodiments, each round of the anthracycline administrations comprises a plurality of doses of anthracycline administration and wherein the step of administering the effective amount of GDF15 to the subject is performed prior to each round of anthracycline administration.

In some embodiments, each round of the anthracycline administration comprises a plurality of doses of anthracycline administration and wherein the step of administering the effective amount of GDF15 to the subject is performed prior to each dose of anthracycline administration.

In some embodiments, the chemotherapy treatment comprises a plurality of rounds of anthracycline administration.

In some embodiments, the anthracycline is selected from the group consisting of doxorubicin, epirubicin, daunorubicin, and idarubicin. In some embodiments, the anthracycline is doxorubicin. In some embodiments, the effective amount is a human equivalent dose of about 0.5 mg/kg in vivo. In some embodiments, the administration of GDF15 is performed about 24 hours prior to the chemotherapy treatment.

In some embodiments, the GDF15 is or comprises a recombinant human GDF15. In some embodiments, the GDF15 essentially consists of a recombinant human GDF15. In some embodiments, the GDF15 consists of a recombinant human GDF15.

In some embodiments, the GDF15 comprises an amino acid sequence SEQ ID NO:1, or a functional variant or homolog thereof. In one embodiment, the GDF15 essentially consists of an amino acid sequence SEQ ID NO:1. In some embodiments, the GDF15 consists of an amino acid sequence SEQ ID NO:1. In some embodiments, the GDF15 essentially consists of an amino acid sequence with at least 90%, 91%, 92%, 93%, 94%, 95%, 96%, 97%, 98%, 99% or 100% homology with SEQ ID NO:1.

In some embodiments, the disease, condition or disorder is selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death. In some embodiments, the disease, condition or disorder is a known complication of cancer treatment, such as chemotherapy (e.g., anthracyclines).

In another aspect, provided is a method of treating or preventing cancer in a subject, comprising the steps of:
(a) administering at least one round of a first composition comprising Growth Differentiation Factor 15 (GDF15), or a functional variant or homolog thereof, to the subject; and
(b) administering at least one round of a second composition comprising anthracycline to the subject.

In some embodiments, step (a) is performed prior to step (b).

In some embodiments, steps (a) and (b) together are performed more than one time. In one example, a plurality of rounds of a first composition comprising Growth Differentiation Factor 15 (GDF15), or a functional variant or homolog thereof, is administered to the subject prior to administering a plurality of rounds of a second composition comprising anthracycline to the subject. In another one example, one single round of a first composition comprising Growth Differentiation Factor 15 (GDF15), or a functional variant or homolog thereof, is administered to the subject prior to each round of a plurality of rounds of a second composition comprising anthracycline to the subject.

In some embodiments, the anthracycline is selected from the group consisting of doxorubicin, epirubicin, daunorubicin, and idarubicin or a functional variant or homolog thereof. In one embodiment, the anthracycline is doxorubicin or a functional variant or homolog thereof. In some embodiments, the first composition has a first human equivalent dose of about 0.5 mg/kg and the composition has a second human equivalent dose about 5 mg/kg. In some embodiments, the ratio of the first human equivalent dose to the second human equivalent dose about 1:10. In some embodiments, the second composition has a single dose of about 1.2-2.4 mg/kg. In some embodiments, the second composition has three divided doses of about 0.4-0.8 mg/kg.

In some embodiments, the GDF15 or functional variant or homolog thereof is a recombinant human GDF15.

In some embodiments, the GDF15 comprises an amino acid sequence of SEQ ID NO:1, or a functional variant or homolog thereof. In some embodiments, the GDF15 essentially consists of an amino acid sequence SEQ ID NO: 1. In some embodiments, the GDF15 consists of an amino acid sequence SEQ ID NO:1. In some embodiments, the GDF15 costs essentially of or consists of an amino acid sequence with at least 90%, 91%, 92%, 93%, 94%, 95%, 96%, 97%, 98%, 99% or 100% homology with SEQ ID NO:1.

In another aspect, provided is a method of treating or preventing a disease, condition or disorder requiring chemotherapy treatment in a subject in need thereof, comprising the step of administering an effective amount of GDF15 to the subject receiving the chemotherapy treatment.

In some embodiments, the effective amount of GDF15 is administered prior to the chemotherapy treatment.

In some embodiments, the chemotherapy treatment comprises at least one round of anthracycline administration, wherein the step of administering the effective amount of GDF15 to the subject is performed prior to each round of anthracycline administration.

In some embodiments, the anthracycline is selected from the group consisting of doxorubicin, epirubicin, daunorubicin, and idarubicin or a functional variant or homolog thereof. In some embodiments, the anthracycline is doxorubicin, or a functional variant or homolog thereof.

In some embodiments, the GDF15 comprises an amino acid sequence of SEQ ID NO:1, or a functional variant or homolog thereof.

In another aspect, provided is a kit for treating preventing or treating a subject suffering from cancer, comprising:
a first composition comprising anthracycline; and
a second composition comprising GDF15.

In some embodiments, the anthracycline is selected from the group consisting of doxorubicin, epirubicin, daunorubicin, and idarubicin or a functional variant or homolog thereof. In one embodiment, the anthracycline is doxorubicin, or a functional variant or homolog thereof.

In some embodiments, the GDF15 comprises an amino acid sequence of SEQ ID NO:1, or a functional variant or homolog thereof. In some embodiments, the GDF15 consists essentially of an amino acid sequence SEQ ID NO:1. In some embodiments, the GDF15 consists of an amino acid sequence SEQ ID NO: 1. In some embodiments, the GDF15 consists essentially of or consists of an amino acid sequence with at least 90%, 91%, 92%, 93%, 94%, 95%, 96%, 97%, 98%, 99% or 100% homology with SEQ ID NO:1.

In another aspect, provided is a use of a pharmaceutical composition comprising GDF15, or a functional variant or homolog thereof, for preventing or treating one or more diseases, conditions or disorders resulting from a chemotherapy treatment.

In some embodiments, the chemotherapy treatment comprises administering anthracycline.

In some embodiments, the anthracycline is selected from the group consisting of doxorubicin, epirubicin, daunorubicin, and idarubicin or a functional variant or homolog thereof. In some embodiments, the anthracycline is doxorubicin, or a functional variant or homolog thereof.

In some embodiments, the anthracycline is doxorubicin.

In some embodiments, the GDF15 is a recombinant human GDF15.

In some embodiments, the GDF15 comprises an amino acid sequence SEQ ID NO:1. In some embodiments, the GDF15 consists essentially of an amino acid sequence SEQ ID NO: 1. In some embodiments, the GDF15 consists of an amino acid sequence SEQ ID NO:1. In some embodiments, the GDF15 consists essentially of or consists of an amino acid sequence with at least 90%, 91%, 92%, 93%, 94%, 95%, 96%, 97%, 98%, 99% or 100% homology with SEQ ID NO:1.

In some embodiments, the diseases, conditions or disorders are selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death.

In another aspect, provided is a use of a composition for preventing or treating anthracycline-associated cardiotoxicity, cardiomyopathy and/or heart failure, wherein the composition comprises GDF15, or a functional variant or homolog thereof.

In some embodiments, the anthracycline is selected from the group consisting of doxorubicin, epirubicin, daunorubicin, and idarubicin or a functional variant or homolog thereof. In some embodiments, the anthracycline is doxorubicin, or a functional variant or homolog thereof.

In some embodiments, the anthracycline is doxorubicin.

In some embodiments, the GDF15 is a recombinant human GDF15.

In some embodiments, the GDF15 comprises an amino acid sequence SEQ ID NO:1, or a functional variant or homolog thereof. In one embodiment, the GDF15 essentially consists of an amino acid sequence SEQ ID NO:1. In one embodiment, the GDF15 consists of an amino acid sequence SEQ ID NO:1. In one embodiment, the GDF15 essentially consists of or consists of an amino acid sequence with at least 90%, 91%, 92%, 93%, 94%, 95%, 96%, 97%, 98%, 99% or 100% homology with SEQ ID NO:1.

In another aspect, provided is a use of a composition in the manufacture of a medicament for preventing or treating one or more diseases, conditions or disorders resulting from chemotherapy treatment, wherein the composition comprises GDF15, or a functional variant or homolog thereof. In some embodiments, wherein the GDF15 comprises an amino acid sequence SEQ ID NO:1, or a functional variant or homolog thereof. In some embodiments, the GDF15 essentially consists of an amino acid sequence SEQ ID NO:1. In some embodiments, the GDF15 consists of an amino acid sequence SEQ ID NO:1. In some embodiments, the GDF15 essentially consists of or consists of an amino acid sequence with at least 90%, 91%, 92%, 93%, 94%, 95%, 96%, 97%, 98%, 99% or 100% homology with SEQ ID NO:1.

In some embodiments, the chemotherapy treatment comprises anthracycline. In some embodiments, the chemotherapy treatment comprises administering at least one round of anthracycline.

In some embodiments, the anthracycline is selected from the group consisting of doxorubicin, epirubicin, daunorubicin, and idarubicin or a functional variant or homolog thereof. In some embodiments, the anthracycline is doxorubicin, or a functional variant or homolog thereof.

In some embodiments, the anthracycline is doxorubicin.

In some embodiments, the GDF15 is a recombinant human GDF15.

In some embodiments, the GDF15 comprises an amino acid sequence SEQ ID NO:1. In some embodiments, the GDF15 essentially consists of an amino acid sequence SEQ ID NO: 1. In some embodiments, the GDF15 consists of an amino acid sequence SEQ ID NO:1. In some embodiments, the GDF15 essentially consists of or consists of an amino acid sequence with at least 90%, 91%, 92%, 93%, 94%, 95%, 96%, 97%, 98%, 99% or 100% homology with SEQ ID NO:1.

In some embodiments, the diseases, conditions or disorders resulting from chemotherapy treatment are selected from the group consisting of cardiotoxicity, cardiomyopathy, cardiac dysfunction, myofibrillar disruption, hypertension, vascular dysfunction, mitochondrial damage, mitochondrial dysfunction, sarcomere disruption, myocardial injury, myocardial tissue loss, cardiac fibrosis, cardiomyocyte apoptosis, cardiomyocyte death, heart failure, shock, multiorgan dysfunction, and death.

In another aspect, provided is a method of increasing viability of a cardiac cell subject to anthracycline exposure comprising the step of contacting the cardiac cell with GDF15 or a functional variant or homolog thereof prior to the anthracycline exposure.

Another aspect provides a method of reducing mitochondrial dysfunction or damage caused by anthracycline exposure in a cardiac cell comprising the step of contacting the cardiac cell with GDF15 or a functional variant or homolog thereof prior to the anthracycline exposure. In some embodiments, the GDF15 essentially consists of an amino acid sequence SEQ ID NO:1. In some embodiments, the GDF15 consists of an amino acid sequence SEQ ID NO: 1. In some embodiments, the GDF15 essentially consists of or consists of an amino acid sequence with at least 90%, 91%, 92%, 93%, 94%, 95%, 96%, 97%, 98%, 99% or 100% homology with SEQ ID NO:1.

In some embodiments, the mitochondrial dysfunction or damage causes cardiomyocyte apoptosis.

In another aspect, provided is a unit dosage form or a composition for treating or preventing a disease, condition, or disorder resulting from or exacerbated by chemotherapy treatment in a subject, comprising recombinant human GDF15 and a pharmaceutically acceptable salt or carrier thereof. In some embodiments, the GDF15 essentially consists of an amino acid sequence SEQ ID NO:1. In some embodiments, the GDF15 consists of an amino acid sequence SEQ ID NO: 1. In some embodiments, the GDF15 essentially consists of or consists of an amino acid sequence with at least 90%, 91%, 92%, 93%, 94%, 95%, 96%, 97%, 98%, 99% or 100% homology with SEQ ID NO:1.

EXAMPLES

Example 1

Materials & Methods

1. Materials 1.1. Recombinant Human Growth Differentiation Factor 15 (GDF-15)/MIC-1

In the following examples, a commercially available recombinant human GDF-15 protein (PeproTech, Inc.) was used for an example composition. The detailed information is listed in Table 1.

TABLE 1

Example recombinant human GDF-15 protein used for experiment.

| | |
|---|---|
| Manufacturer/vendor: | PeproTech, Inc. |
| Catalog number: | 120-28C |
| Source: | CHO cell-derived |
| Amino acid sequence (monomer): | ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI (SEQ ID NO: 1) |

TABLE 1-continued

Example recombinant human GDF-15 protein used for experiment.

| | |
|---|---|
| Molecular weight: | 24.6 kDa |
| Accession number: | Q99988 |
| Gene ID: | 9518 |
| Cross reactivity cited in references: | human, mouse |

Example 2

2. Preparation of Reagents

Recombinant human GDF15/MIC-1 protein (CHO-derived) was purchased from PeproTech Inc. (Cranbury, USA) and described in Example 1. Doxorubicin hydrochloride ((8S,10S)-10-[(3-Amino-2,3,6-trideoxy-L-lyxohexopyranosyl)oxy]-7,8,9,10-tetrahydro-6,8,11-trihydroxy-8-(hydroxyacetyl)-1-methoxynaphthacene-5,12-dione hydrochloride; CAS number 25316-40-9) and dexrazoxane hydrochloride (4,4'-[(1S)-1-Methyl-1,2-ethanediyl]bis-2,6-piperazinedione hydrochloride; PubChem identifier number 71384) were purchased from Abcam (Cambridge, UK). For in vitro studies, solid lyophilized powder of these two drugs were solubilized at the recommended concentrations in sterile water, and separate aliquots were made and frozen until thawing prior to addition to cell cultures. For in vivo studies, all agents were dissolved in 0.09% normal saline according to the required concentrations (doxorubicin, 5 mg/kg; GDF15, 0.5 mg/kg; dexrazoxane, 100 mg/kg), and the final volume of each intraperitoneal injection was 100 μl. The recommended dose ratio of dexrazoxane to doxorubicin was 10 to 1. In the following examples, 5 mg/kg of doxorubicin was used which correspond to 50 mg/kg of dexrazoxane. The FDA recommends that dexrazoxane be injected within 0.5 hour prior to doxorubicin infusion in individuals. This was followed in the same manner when applying to the test animals.

Example 3

3. Cell Culture 3.1. Maintenance and Passaging of Human Embryonic Stem Cells (hESCs)

Human embryonic stem cells (hESCs) of line H7 were purchased from WiCell Research Institute, Inc. (Madison, Wisconsin, USA) and cultured in E8 medium (Thermo Fisher Scientific, USA). Media were replaced daily, unless specified. Cells were passaged at approximately 80-95% confluency. E8 media were changed 1 hour prior to passage, followed by rinsing once with Dulbecco's phosphate buffered saline devoid of calcium and magnesium supplement (DPBS-/-) (Thermo Fisher Scientific, USA). 0.5 mM EDTA (Thermo Fisher Scientific, USA) were added for 5-7 minutes at room temperature until the cells appeared rounded, and EDTA was removed by aspiration. 1 ml of E8 media with Y27632 (1 μl/ml, Selleck Chemicals, Texas, USA), a specific inhibitor of ROCK (p160ROCK), was added, and cells were dislodged gently. The mixture was removed and placed on a 6-well plate coated with Matrigel (Corning Inc., USA) at an optimized density (1:5/1:7 for three days, 1:6/1:8 for four days). The E8+Y27632 media were changed to the E8 medium (without ROCK inhibitor) within 24 hours and replaced daily.

3.2. Cardiomyocyte Differentiation

When hESCs reached approximately 80% confluency, they were designated Day 0. On Day 0, E8 media were changed 1 hour prior to initiation of the differentiation procedure. Cells were treated with 6 μM CHIR99021 (Selleck Chemicals Inc.), an inhibitor of GSK-3, in RPMI-1640 (Thermo Fisher Scientific, USA) and B27-supplement (Thermo Fisher Scientific, USA) for 2 days. On Day 2, media were changed to RPMI-1640 and Gibco B27-supplement (Thermo Fisher Scientific, USA). On Day 3, media were changed RPMI-1640 with 5 μM IWR-1 (Sigma) and B27-supplement, and allowed to incubate for 48 hours. Spent media were discarded on Day 5, cells were refreshed with RPMI-1640 and B27-supplement, and allowed to incubate for another 48 hours until Day 7. On Day 7, media were changed from RPMI-1640 and B27− supplement to RPMI-1640 and B27+ supplement (Thermo Fisher Scientific, USA). Daily media change was completed at approximately the same time (within 1-hour difference). From Day 7 onwards, the differentiated cells were cultured in RPMI and B27+ supplement, and media were changed every 2 days from then on until use. Beating hESC-cardiomyocytes (hESC-CMs) were seen by Day 7. Efficiency of differentiation was estimated at approximately 90%.

3.3. PrestoBlue™ Cell Viability Analysis

Viability of hESC-CMs was assessed using PrestoBlue (Thermo Fisher Scientific, USA). hESC-CMs in suspension were seeded at a density of 15,000 cells per well on 96-well flat-bottom microtiter plates and cultured at 37° C. in a humidified 5% $CO_2$ atmosphere. The B27+/RPMI-1640 media with Y27632 were changed to B27+/RPMI–1640 media within 24 hours. Cells were then incubated in B27+/RPMI–1640 without supplement for at least 72 hours. PrestoBlue was diluted in a ratio of 1:10 in B27+/RPMI–1640 media and incubated with the cells at 37° C. for 30 minutes. After incubation, fluorescence reading was performed at excitation and emission wavelengths of 530 nm and 590 nm, respectively, using the Synergy HTX Multi-Mode microplate reader (Agilent Technologies, Inc., USA).

3.4. Dose-Response Analysis of Optimal GDF15 Concentration

Six logarithmic concentrations of GDF15 were initially used to identify the optimal dose for cytoprotection: 0.1 ng/ml, 1 ng/ml, 10 ng/ml, 100 ng/ml, 1,000 ng/ml (1 ug/ml), and 10,000 ng/ml (10 ug/ml). Further refinement of dose response was subsequently achieved using concentrations at 100 ng/ml, 200 ng/ml, and 300 ng/ml. The optimal time point (see below) of 24 hours was selected. Doxorubicin at 1.5 μM was used to induce cytotoxicity.

3.5. Time-Response Analysis of Optimal Timing of GDF15 Pretreatment hESC-CMs were pretreated with GDF15 for 1 hour, 6 hours, 24 hours, 48 hours, or 72 hours ("pretreatment"), followed by exposure to 1.5 μM doxorubicin alone for a further 24 hours. A second set of experiments involved pretreatment of hESC-CMs for 1 hour, 6 hours, 24 hours, 48 hours, or 72 hours, followed by removal of the media containing GDF15, and coincubation of hESC-CMs with both GDF15 and doxorubicin for another 24h ("pre/cotreatment"). The efficacy of GDF15 in protecting cardiomyocytes was assessed by cell viability analysis using PrestoBlue.

3.6. Evaluation of Mitochondrial Function

Mitochondrial membrane potential (MMP) as a measure of mitochondrial function and viability was assessed using tetramethylrhodamine ethyl ester (TMRE) (Thermo Fisher Scientific, USA), a cell-permeant cationic fluorescent dye that is readily taken up by viable mitochondria. hESC-CMs seeded at 15,000 cells per well on a 96-well flat-bottom microtiter plate were cultured at 37° C. in a humidified 5% $CO_2$ atmosphere for at least 3 days before MMP measurement. TMRE dye was applied at 50 nM for 20 minutes in B27+/RPMI–1640 media, followed by fluorescence reading at excitation and emission wavelengths of 485 nm and 528 nm, respectively, using the Synergy HTX Multi-Mode microplate reader.

3.7. Mitochondrial Morphology Analysis

To evaluate mitochondrial morphology as a surrogate of cell and mitochondrial viability, hESC-CMs were incubated in B27+/RPMI–1640 media containing 50 nmol/L MitoTracker Deep Red (MTDR) (Thermo Fisher Scientific, USA), and 1 μg/ml Hoechst 33342 (Thermo Fisher Scientific, USA) for 20 minutes. Microscopic images were acquired using DMi8s Research Inverted Thunder Imager Live Cell System (Leica, Germany). For MTDR and Hoechst 33342 imaging, excitation wavelengths of 540 nm and 480 nm, respectively, were used. Mitochondrial morphology was classified into three categories: i) elongated, ii) punctate, and iii) perinuclear. Nuclear morphology was classified as either condensed or normal.

3.8. Immunocytochemistry hESC-CMs were permeabilized using 0.1% Triton X-100 (Thermo Fisher Scientific, USA). After permeabilizing for 15 minutes, cells were washed three times in PBS, and further permeabilization was blocked by incubating cells in PBS with 10% FBS (Hyclone, USA) for 1 hour at room temperature. Cells were incubated with the primary anti-actinin antibody (1:400) (Abcam, UK) and diluted in PBS with 10% FBS overnight. Cells were then washed three times with PBS and incubated with a goat anti-mouse IgG1 secondary antibody (1:1000 diluted in PBS with 10% FBS) (Thermo Fisher Scientific, USA) for 1 hour at room temperature. Finally, cells were washed twice with PBS and mounted using ibidi mounting medium with DAPI (Ibidi, Germany). Microscopic images were acquired using the DMi8s Research Inverted Thunder Imager Live Cell System (Leica, Germany) at 20×, 40×, and 100× magnification.

3.9. RNA Isolation, cDNA Synthesis, and Real-Time Quantitative Polymerase Chain Reaction RNA was extracted using TRIzol™ Reagent (Thermo Fisher Scientific, USA) as per manufacturer's protocol. RNase-free reagents and consumables were used. RNA concentration and A260/280 ratio were determined using Synergy HTX Multi-Mode microplate reader (Agilent Technologies, USA).

cDNA was synthesized using the PrimeScript™ RT Master Mix (Takara, Japan) for real-time quantitative polymerase chain reaction (qPCR). Briefly, reverse transcription used 2 μl of 5× PrimeScript™ RT Master Mix, 0.5 μg of total RNA, and RNase-free $dH_2O$ added to total mixture volume of 10 μl. The reaction was carried out at 37° C. for 15 minutes and 85° C. for 5 seconds.

qPCR was performed using SYBR Green Master Mix (Promega, USA) as per manufacturer's protocol. A total reaction volume of 10 μl included 5 μl GoTaq® qPCR Master Mix 2×, 0.3 μl 10 nmol/L primers mix, and 30 ng cDNA template. The qPCR condition was: 1 cycle of 95° C. for 2 minutes, 40 cycles of 95° C. for 3 seconds, and 60° C. for 30 seconds. Expression level of genes was quantified using the $2^{-\Delta\Delta CT}$ method on a ABI QuantStudio 12-Flex QPCR System W/96 Fast & 384 (Thermo Fisher Scientific, USA). Primer sequences used were summarized as follows for the respective gene sequences (Table 2).

TABLE 2

Primer sequences for ATP5F1B, COX6B1, NDUFAB1, and SDHA.

| Primer name | Primer sequences (5' to 3') | Sequence ID NO. |
|---|---|---|
| ATP5F1B, F | CTGGTGTTGGTGAGAGGACC | SEQ ID NO: 2 |
| ATP5F1B, R | CAGACACCTCTGAACCAGCC | SEQ ID NO: 3 |
| COX6B1, F | CGGGGTGCCTTTAGGATTCA | SEQ ID NO: 4 |
| COX6B1, R | TTCTGACAGCGGTGGAAGTC | SEQ ID NO: 5 |
| NDUFAB1, F | CGCGCAGGTTCCTGGTAG | SEQ ID NO: 6 |
| NDUFAB1, R | GTCCTGGATGCCCTCTAACG | SEQ ID NO: 7 |
| SDHA, F | TTGCAGCACAGGGAGGAATC | SEQ ID NO: 8 |
| SDHA, R | CCGTCATGTAGTGGATGGCA | SEQ ID NO: 9 |

3.10 Flow Cytometry

To dissociate cultured hESC-CMs, cells were washed with DPBS−/−once and incubated with 1 ml per well of trypsin-EDTA (0.05%) at 37° C. for ~5-15 minutes. Thereafter the same volume of neutralization medium (RPMI-1640 medium supplemented with 10% FBS) was added to neutralize digestion. Dissociated cells were collected and transferred to a 15-ml tube, and centrifuged at 300×g for 4 minutes at 4° C. Supernatant was discarded. Anti-cardiac troponin T (cTnT) monoclonal antibody (Abcam, UK) was applied to cells for 1 hour at 4° C. Cells were then washed with wash buffer (0.5% BSA and 0.1% Triton X-100 in DPBS−/−) once and incubated with goat anti-mouse IgG1 secondary antibody (Thermo Fisher Scientific, USA), or IgG1 isotype control, and then washed once again with wash buffer. Cardiac troponin-positive cells were gated against <2% of the isotype negative control. Flow cytometric analysis was performed using a CytoFLEX Flow Cytometer (Beckman Coulter, USA) or Attune NxT Flow Cytometer (Thermo Fisher Scientific, USA). FlowJo version 10.6.2 software was used for data analysis.

Example 4

4. Animal Research 4.1. Ethics Statement, and Housing and Wellbeing of Animals

All animal research was performed in accordance with the Guidelines for Care and Use of Laboratory Animals, and the study was approved by the University Animal Experimentation Ethics Committee of The Chinese University of Hong Kong (CUHK), Hong Kong SAR, China.

Ten- to twelve-week old C57BL/6J male mice were purchased from the Laboratory Animal Services Centre of CUHK. They were maintained in specific pathogen-free facility of the CUHK Laboratory Animal Services Centre Research Unit at Prince of Wales Hospital with free access to food and water and maintained in a light/night cycle of 12 hours/12 hours. All mice were fed a standard diet.

4.2. Noninvasive Blood Pressure Measurements in Mice

Blood pressure of animals was measured using the non-invasive CODA® High Throughput System (Torrington, USA) in accordance with the manufacturer's instructions. Measurement platform was prewarmed and maintained at 33-35° C. O-cuffs and VPR-cuffs were used as instructed. Blood pressure of each mouse was measured for at least three cycles. Mice were released and returned to their cages immediately after measurement. Blood pressure was measured twice, once at the beginning of the experiment and once before sacrifice.

4.3. Measurements of Animals' Body Weight, Heart Weight, and Tibia Length

The body weight of each mouse was recorded weekly, before each doxorubicin injection and before sacrifice. At the end of experiment, all mice were euthanized with sodium pentobarbital 100 mg/kg administered intraperitoneally, and the hearts were excised immediately. The tibia of the mice were carefully dissected and its length was measured.

4.4. Induction of Doxorubicin Cardiotoxicity in Mice

To induce cardiotoxicity in the mouse, four weekly intraperitoneal injections of doxorubicin at 5 mg/kg were administered. After one dose of doxorubicin at 5-6 mg/kg in a mouse, the level of exposure has been estimated to be similar to that of a human individual being given a standard dose of doxorubicin at approximately 60 mg/m$^2$. Previous studies have shown that mice injected with doxorubicin once a week at 5 mg/kg for four weeks developed cardiotoxicity, as evidenced by decreased ventricular ejection fraction, cardiomyocyte apoptosis, histopathological changes consistent with doxorubicin-induced myocardial damage, and increased mortality rate, compared with the control group.

4.5. Histopathologic Analysis 4.5.1. Hematoxylin and Eosin (H&E) Staining

The hearts of mice were collected after sacrifice and fixed in 4% paraformaldehyde overnight, followed by paraffin embedding. Afterwards the hearts were cut into 4 μm thick slices. Sections were deparaffinized and rehydrated using sequential immersion in 100% alcohol, 95% alcohol and 70% alcohol for 15 minutes each. After deparaffinization and rehydration, the slides were placed in hematoxylin solution (Sigma-Aldrich, USA) for 5 minutes, rinsed with dH$_2$O twice for 10 seconds, followed by acid alcohol for 10 seconds to remove excess stain. The slides were then transferred to 0.5% aqueous Eosin Y Solution (Sigma-Aldrich, USA) for 2 minutes, and rinsed with dH$_2$O twice, followed by dehydration in absolute alcohol. Slides were mounted using Permount™ medium (Thermo Fisher Scientific, USA).

4.5.2. Masson's Trichrome Staining for Cardiac Fibrosis

Sections were deparaffinized and rehydrated as previously described (see above 4.4). Then sections were rinsed under running tap water for 10 minutes. Next, sections were washed once in dH$_2$O, then stained in Biebrich scarlet-acid fuchsin solution (Sigma-Aldrich, USA) for 10-15 minutes. Afterwards they were washed in dH$_2$O once. Sections were then covered with a phosphomolybdenum-phosphotungstic acid solution (Sigma-Aldrich, USA) and incubated for 10-15 minutes at room temperature. Next, the solution was removed from the slides, and without rinsing the sections were placed directly in aniline blue solution and stained for 5-10 minutes. Sections were then rinsed once with dH$_2$O, incubated in 1% acetic acid solution for 2-5 minutes, and rinsed again in dH$_2$O. Sections were then dehydrated quickly in 95% ethyl alcohol, and absolute ethyl alcohol and cleared in xylene. Slides were mounted using Permount™ medium.

4.5.3. Analysis of Cardiomyocyte Apoptosis by TUNEL Staining

To visualize cardiomyocyte apoptosis, TUNEL staining was performed according to the manufacturer's instruction (Abcam, UK). Sections were deparaffinized and rehydrated as previously described (see above 4.4). Thereafter sections were overlaid with 100 μl diluted Proteinase K solution (¹⁄₁₀₀ in dH$_2$O) and incubated at 37° C. for 20 minutes. The slides were then rinsed with 1×TBS for 5 minutes. Excess liquid on the slides was gently shaken off and blotted dry. Specimens were covered with 100 μl of 3% H$_2$O$_2$ and incubated at 37° C. for 5 minutes. Slides were rinsed in 1×TBS for 5 minutes, then covered with 100 μl of TdT Equilibration Buffer and incubated for 30 minutes at 37° C. The slides were overlaid with 40 μl of the TdT-labeled reaction immediately, then the coverslips were used to cover the samples and ensure uniform coating of the reaction mixture on the tissue while preventing evaporative loss during incubation. Slides were placed in a humidified chamber at 37° C. for 1.5 hours. Before the next step, the stop buffer was prewarmed to 37° C. to remove the precipitate. The slides were completely immersed in the TBS solution and the coverslips were allowed to slide gently out of the sample while avoiding damage to the specimen. The sections were then rinsed in 1×TBS for 5 minutes. Each specimen was covered with 100 μl of Stop Buffer next and incubated at room temperature for 5 minutes. Afterwards the slides were rinsed again with 1×TBS for 5 minutes, then covered with 100 μl of Blocking Buffer and incubated at room temperature for 10 minutes. Without rinsing, the Blocking Buffer was carefully blotted from the specimen, and the 100 μl of 1× conjugate was immediately applied to the specimen. The slides were allowed to incubate in a humidified chamber at room temperature for 30 minutes, then rinsed with 1×TBS for 5 minutes. Afterwards each specimen was covered with 100 μl of diluted DAB solution and incubated at room temperature for 15 minutes. Finally, the slides were rinsed with dH$_2$O and mounted using Permount™ medium.

4.5.4. Quantitative Analysis of Histopathologic Staining

The image processing and analysis software, ImageJ version 1.53K, was used for evaluation of histopathology from mouse experiments. For Masson's trichrome staining, the acquired images were converted from color to grayscale using ImageJ, the blue-stained collagen were segmented (separated) using thresholding, and the threshold areas in a representative microscopic field were quantified. For TUNEL staining, the nuclei that stained brown were indicative of apoptosis. Cells containing brown staining (TUNEL-positive cells) were counted in a representative microscopic field for each mouse in each group.

Example 5

The following results were obtained by the methods described in Examples 1-4.
Results
5.1 Viability of Human Cardiac Cells Exposed to Anthracycline is Increased by GDF15

Figure 1A:
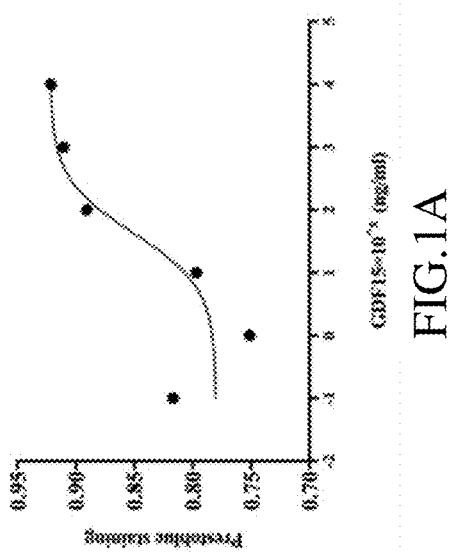
FIG. 1A is a dose-response curve at six logarithmic concentrations of GDF15 using the PrestoBlue™ assay, according to an example embodiment.
Figure 1B:
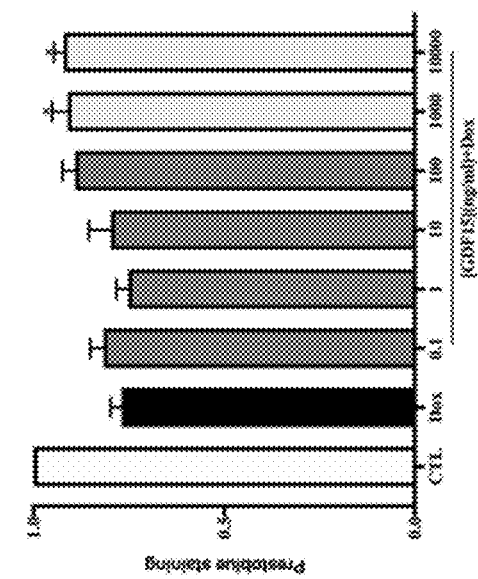
FIG. 1B is the results of a dose finding study of pretreatment with GDF15 at concentrations from 0.1 ng/ml to 10,000 ng/ml before applying doxorubicin, according to an example embodiment.

The following dose-response analyses of optimal GDF15 concentration and time-response analyses of optimal timing of GDF15 pretreatment were performed. Now referring to FIG. 1A, the results showed that GDF15 pretreatment of cultured hESC-CMs for 24 hours before applying doxorubicin resulted in increased cell viability (positive PrestoBlue staining) in a dose-dependent manner (FIG. 1A). Detailed dose finding identified 300 ng/ml to 1000 ng/ml (1 ug/ml) of recombinant human GDF15 protein as the optimal concentration for cytoprotection (FIGS. 1B and 1C). The results indicated that the optimal timing of pretreatment prior to doxorubicin was 24 hours (FIG. 1D). Once hESC-CMs have been primed with GDF15 for 24 hours, the optimal timepoint, its cytoprotective effects persisted (FIG. 1E). Using real-time polymerase chain reaction (PCR), the results showed that the expression of genes important for mitochondrial function were suppressed by doxorubicin but improved in hESC-CMs pretreated with GDF15 prior to doxorubicin exposure (FIG. 1F).

The data represent mean±SEM for n=5 independent experiments (FIGS. 1A-C and F) and n=7 independent experiments (FIGS. 1D-E). One-way ANOVA followed by Dunnett's test was used. *p<0.05 and **p<0.01 for comparison against doxorubicin (Dox) only group. The above results showed that the most efficacious dose and timing of recombinant GDF15 protein administration is 300 ng/ml to 1000 ng/ml (1 ug/ml), approximately 24 hours prior to doxorubicin exposure.

5.2 Mitochondrial Dysfunction and Damage from Anthracycline are Attenuated by GDF15

Figures 2A, 2B, 2C:
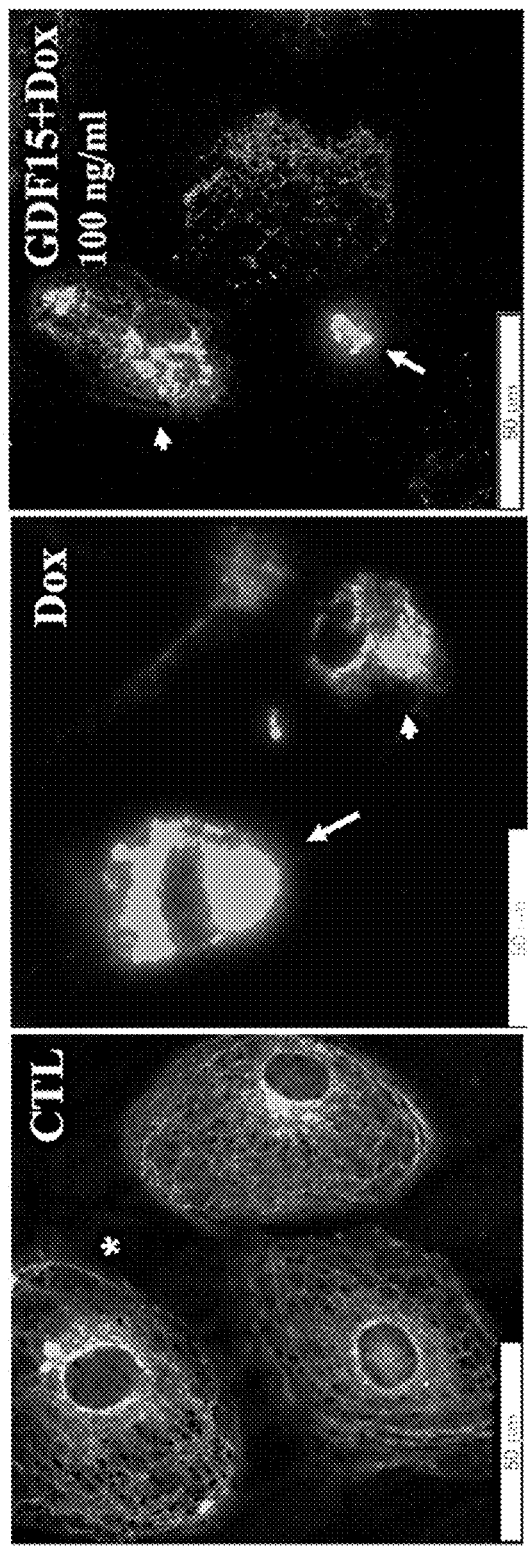
Figure 2H:
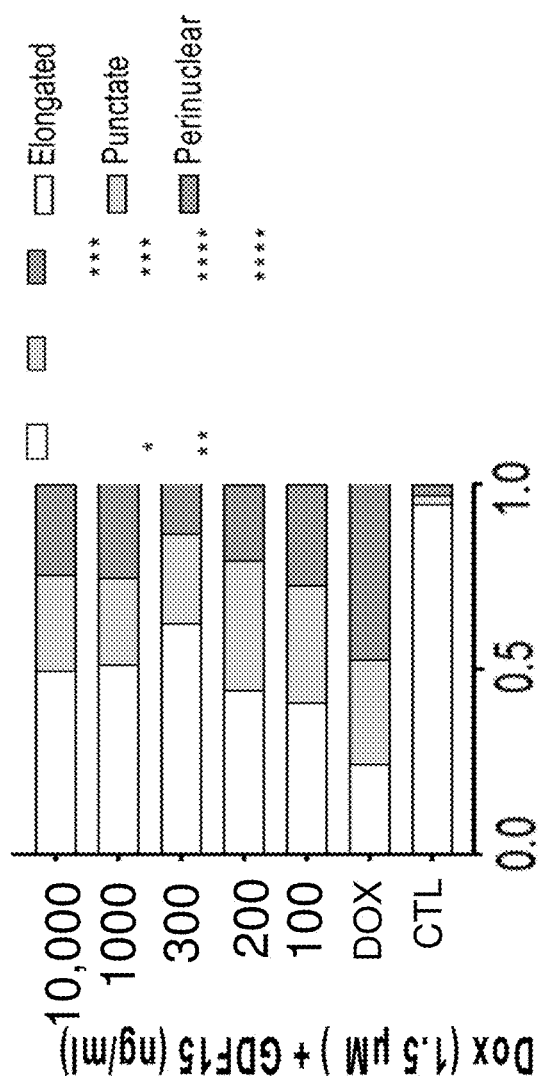
FIG. 2H is a graphical illustration of the proportion of hESC-CMs exposed to Dox with elongated, punctate, and perinuclear mitochondria upon pretreatment with increasing concentrations of human recombinant GDF15, according to an example embodiment.
Figure 2G:
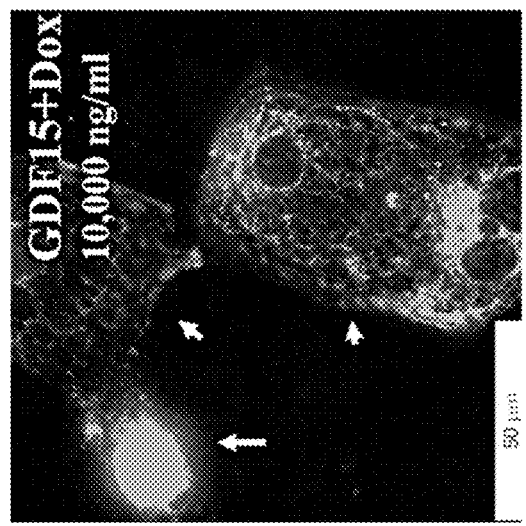
Figures 3D, 3E, 3F:
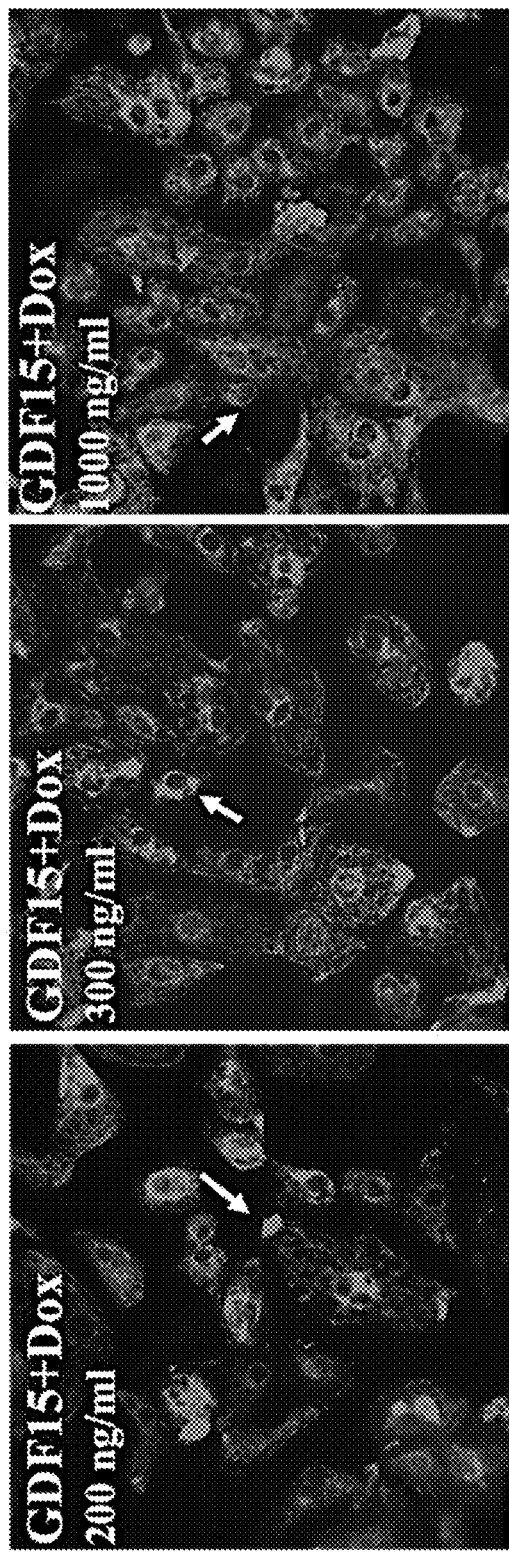
Figure 3H:
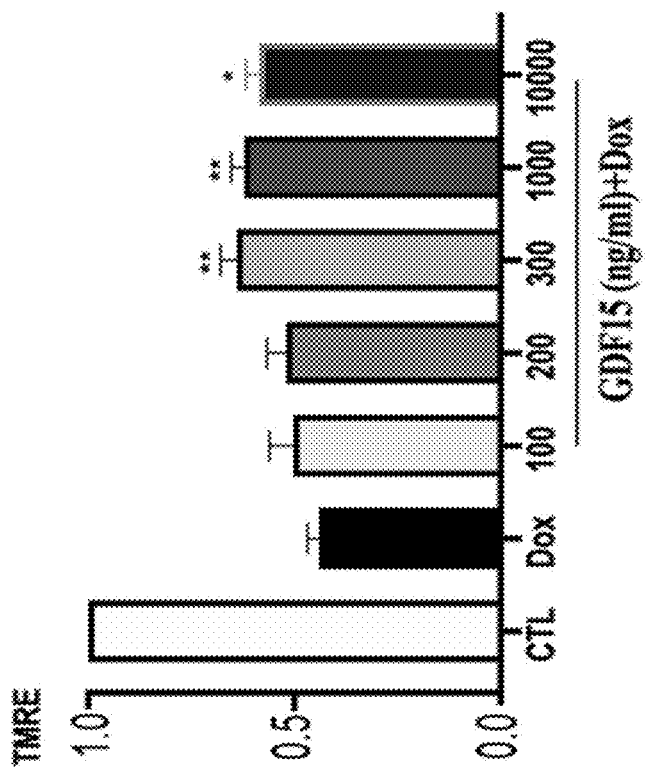
FIG. 3H is a graphical illustration of TMRE integrated density upon pretreatment with increasing concentrations of human recombinant GDF15, according to an example embodiment.
Figure 3G:
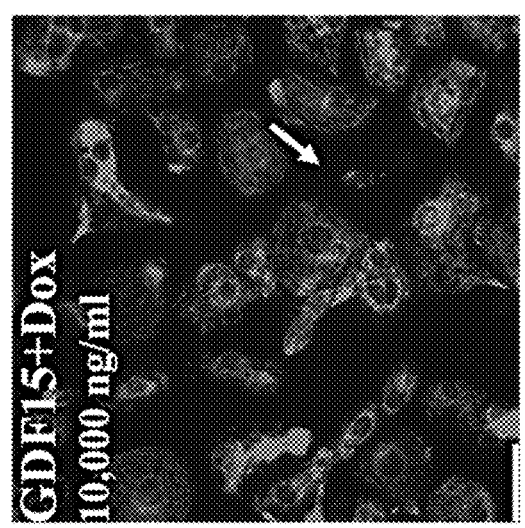

The following results were conducted for assessment of mitochondrial morphology of hESC-CMs treated with and without doxorubicin and GDF15. The results showed that doxorubicin-treated cells (Dox) had markedly reduced elongation compared with the untreated negative control (CTL) (24.5±17.1% vs. 94.6±5.8%), and increased punctation or perinuclear changes (47.3±12.6% vs. 5.4±4.2%) (FIGS. 2A & 2B). The results demonstrated the dose dependency of GDF15 pretreatment and that 300 ng/ml of GDF15 pretreatment provided optimal though partial reversal of abnormal mitochondrial morphology in hESC-CMs exposed to doxorubicin (62.5±11.0% elongated mitochondria and 13.2±14.7% perinuclear mitochondria) (FIGS. 2C-2H). Scale bar indicates a length of 50 Data from random fields were obtained from n=6 independent experiments. Statistical significance was calculated relative to the Dox-treated cells using one-way ANOVA with Dunnett's multiple comparisons test. *p<0.05, p<0.01, *p<0.001, ****p<0.0001.

The results also showed that, at 300 ng/ml of GDF15, mitochondrial membrane potential and function assessed using the TMRE fluorescent dye was better preserved than at other concentrations (FIGS. 3A-H). Scale bar indicates a length of 50 Fluorescence intensity was quantified per microscopic field. Data were obtained from n=6 independent experiments. Statistical significance was calculated relative to the doxorubicin-treated cells using one-way ANOVA with Dunnett's multiple comparisons test such that *p<0.05, p<0.01, *p<0.001, ****p<0.0001.

In summary, the above results showed that mitochondrial dysfunction and damage from anthracycline (Dox) are significantly attenuated by GDF15.

5.3 Cardiomyocyte Apoptosis Following Exposure to Anthracycline is Reduced by GDF15

Figures 4A, 4B, 4C:
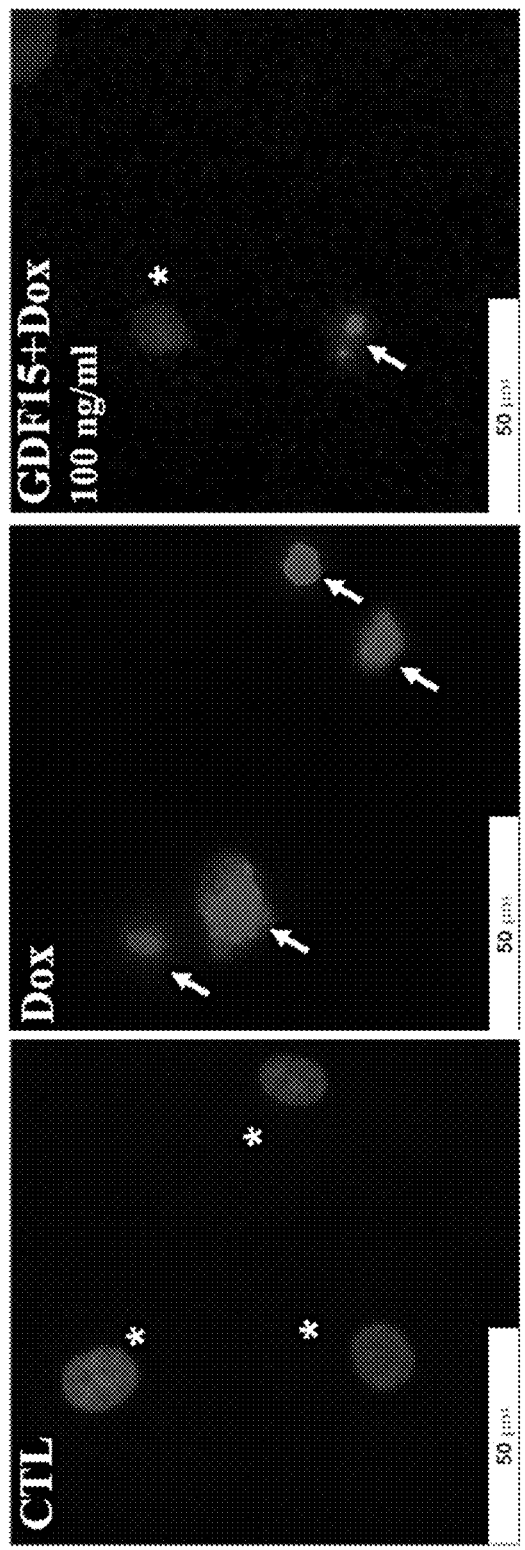

As a measure of cardiomyocyte apoptosis, nuclear condensation was evaluated using Hoechst 33342 nuclear stain in the untreated negative control (CTL) (FIG. 4A), the doxorubicin only group (Dox) (FIG. 4B), and the doxorubicin with GDF15 pretreatment group (GDF15+Dox) over a dose range from 100 to 10,000 ng/ml (FIGS. 4C-G). Compared with the negative control that showed negligible nuclear abnormality, >40% of doxorubicin-treated hESC-CMs displayed nuclear condensation that was markedly reduced to 12.8±1.7% in cells pretreated with 300 ng/ml of GDF15 (FIGS. 4E & 4H). In summary, the above results showed that cardiomyocyte apoptosis following exposure to anthracycline is significantly reduced by GDF15.

5.4 GDF15 has Similar Efficacy to Dexrazoxane in Reducing Cardiac Cytotoxicity.

Figure 5A:
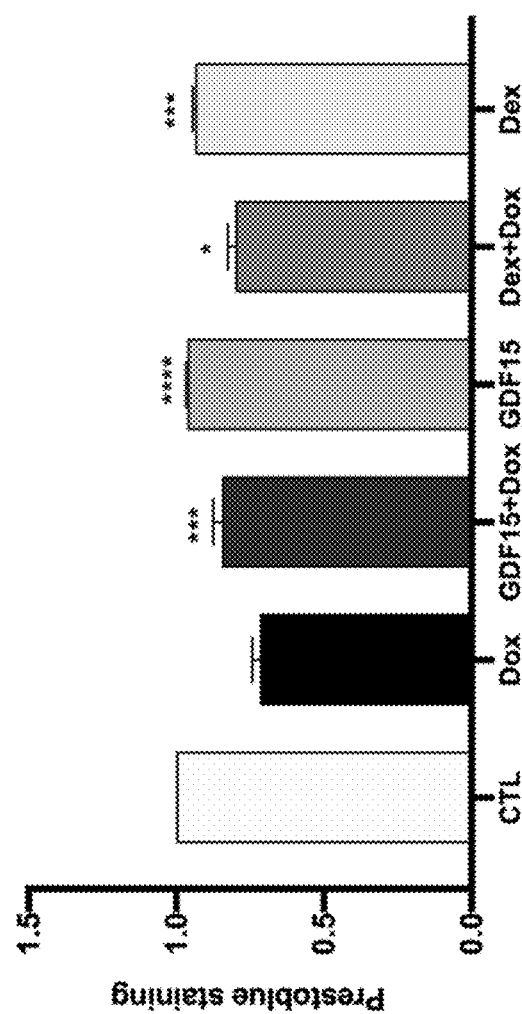
FIG. 5A is a graphical illustration comparing the effects of GDF15 and dexrazoxane (Dex) pretreatment on hESC-CM viability in the presence of Dox using PrestoBlue™ assay, according to an example embodiment.
Figures 5B, 5C:
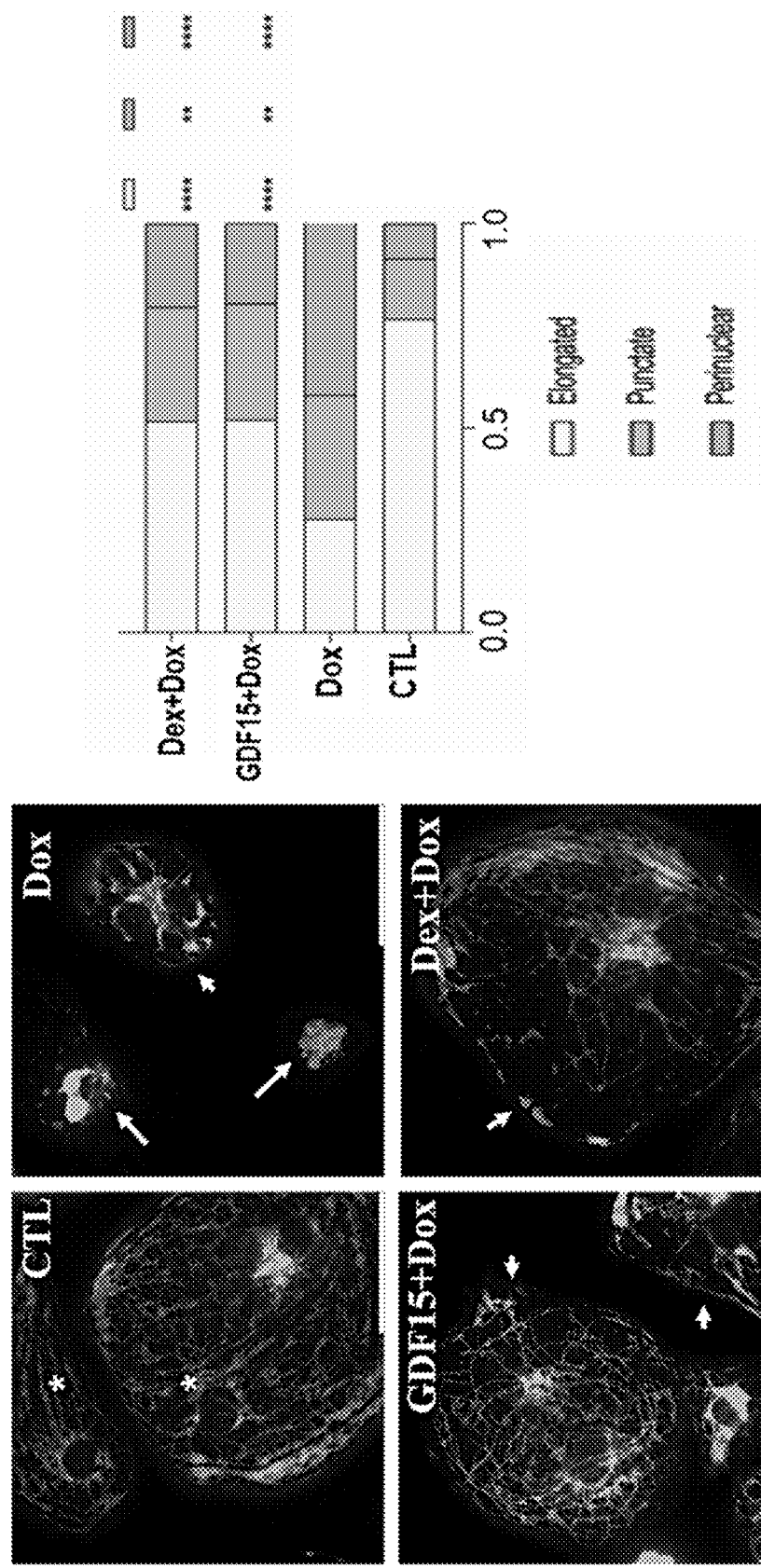
FIGS. 5B-5C are the results of mitochondrial staining using the MTDR dye to quantify and compare the proportion of hESC-CMs exposed to Dox with elongated, punctate, and perinuclear mitochondria upon pretreatment of GDF15 or Dex in the presence of Dox, according to an example embodiment.
Figures 5D, 5E:
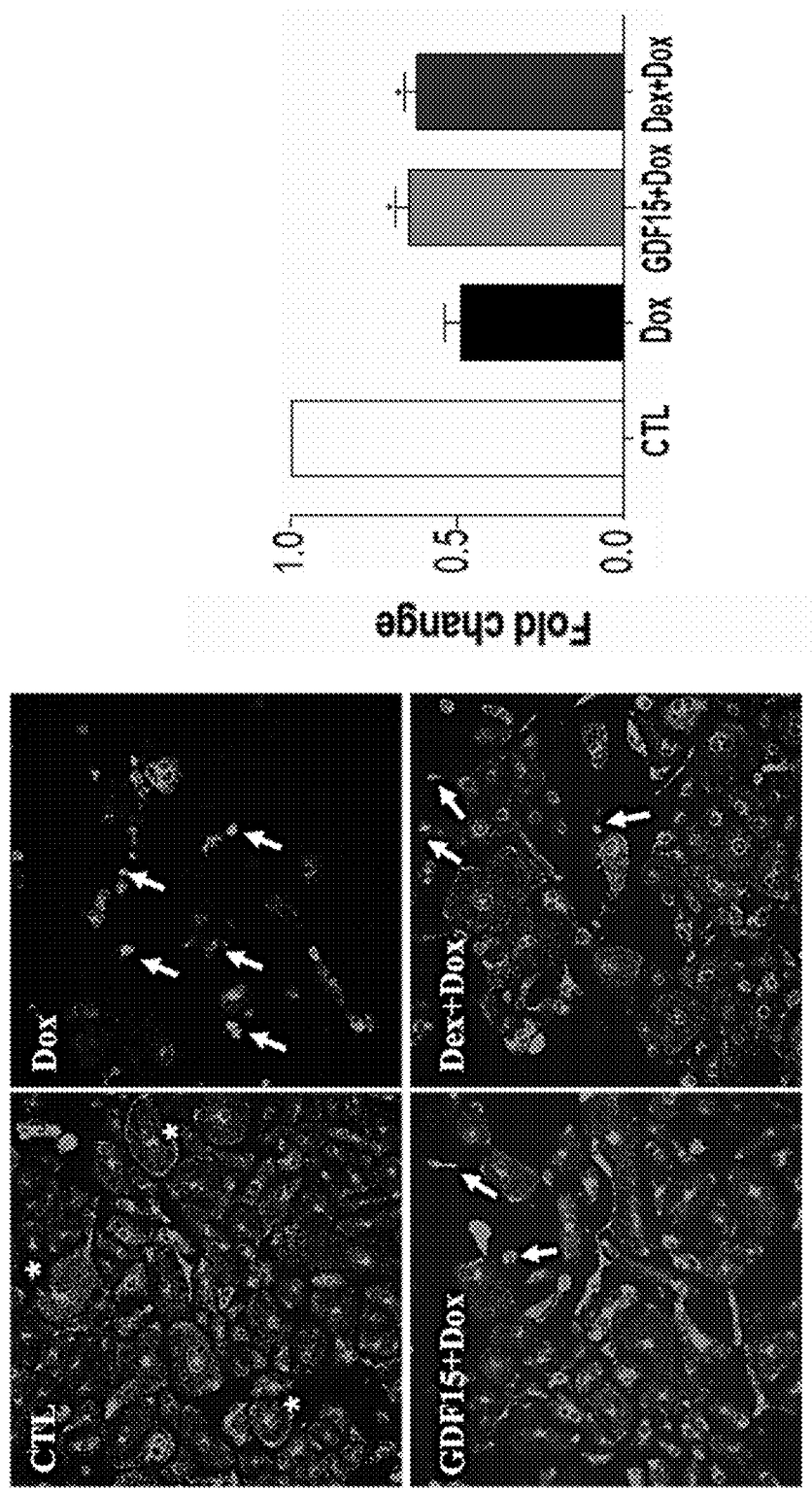
FIGS. 5D-5E are the results of staining with TMRE to assess mitochondrial membrane potential and function in hESC-CMs exposed to Dox upon pretreatment of GDF15 or Dex, according to the same example embodiment as shown in previous figures.
Figures 5F, 5G:
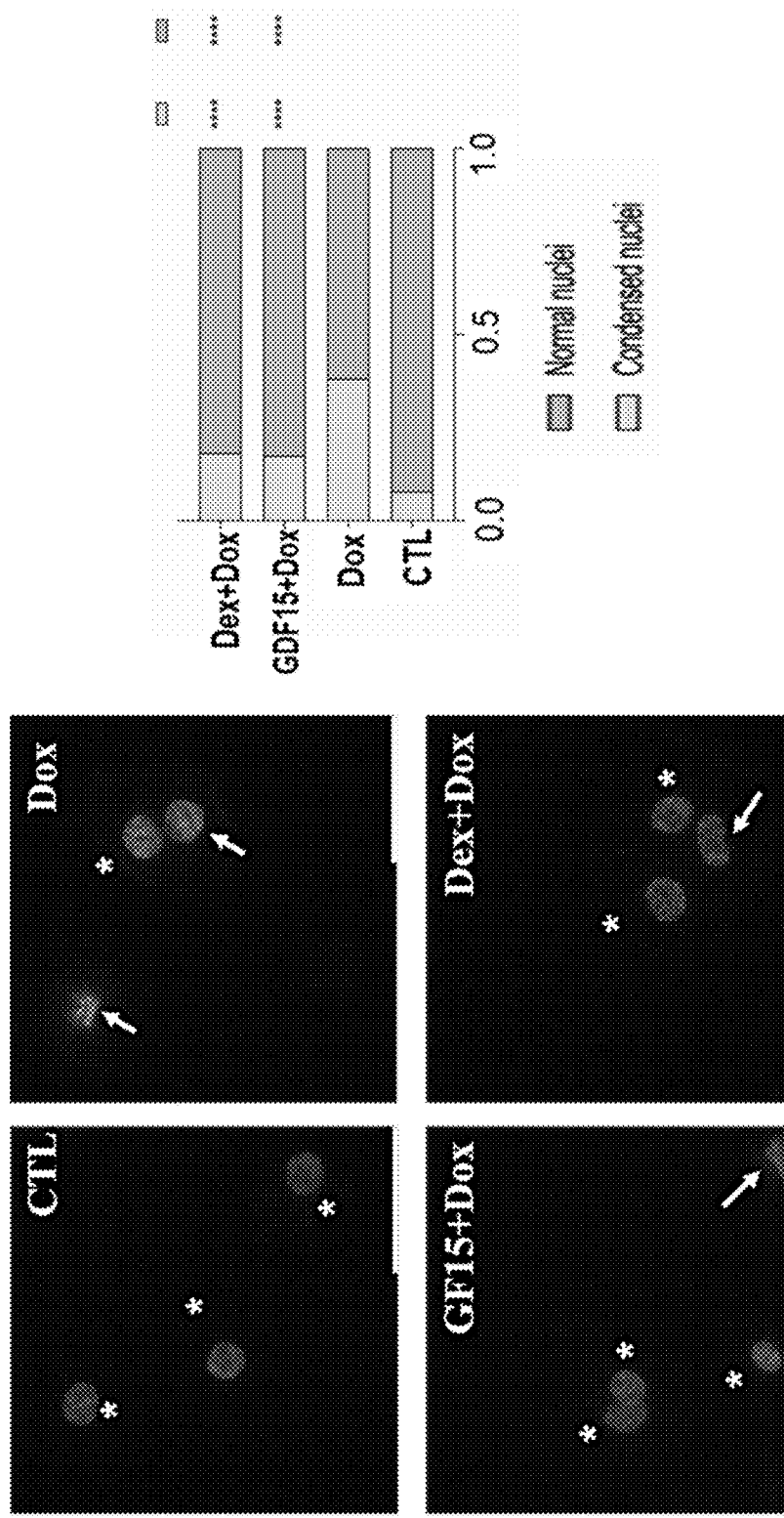
FIGS. 5F-5G are the results of staining with the Hoechst 33342 dye to assess nuclear condensation and morphology, and signs of apoptosis in hESC-CMs exposed to Dox upon pretreatment of GDF15 or Dex, according to an example embodiment.

To benchmark the findings against dexrazoxane, the current available prophylaxis against anthracycline cardiotoxicity, the above evaluations for cell viability were repeated (FIG. 5A) using GDF15 and Dex, respectively, mitochondrial integrity (FIGS. 5B-C), mitochondrial membrane potential (FIGS. 5D-E), and the extent of nuclear condensation as a surrogate marker of apoptosis (FIGS. 5F-G). In all these experiments, recombinant human GDF15 performed similarly to dexrazoxane, and with slightly higher percentage of cell viability (FIGS. 5A-G). Collectively, the results suggested that the cytoprotective action of GDF15 in hESC-CMs are exerted through enhancement of mitochondrial function and suppression of apoptosis.

Figure 5H:
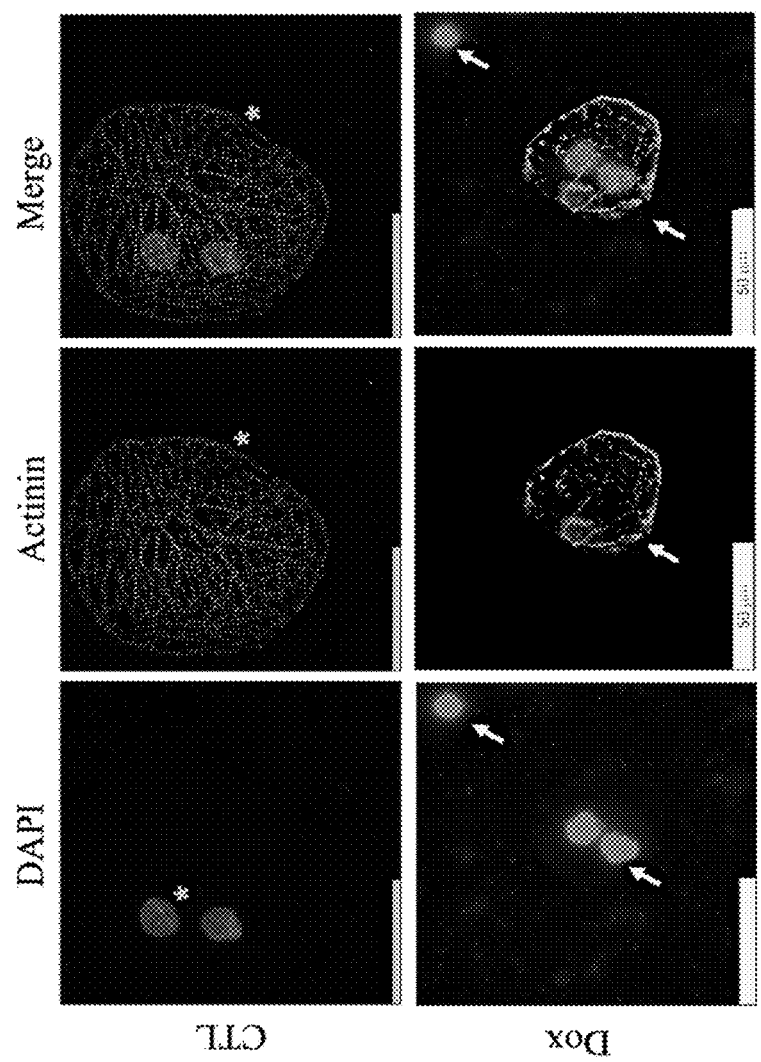
FIGS. 5H-5J are the microscopic images of staining with DAPI and α-actinin to assess sarcomeric integrity in hESC-CMs exposed to Dox upon pretreatment of GDF15 or Dex, according to an example embodiment.
Figure 5I:
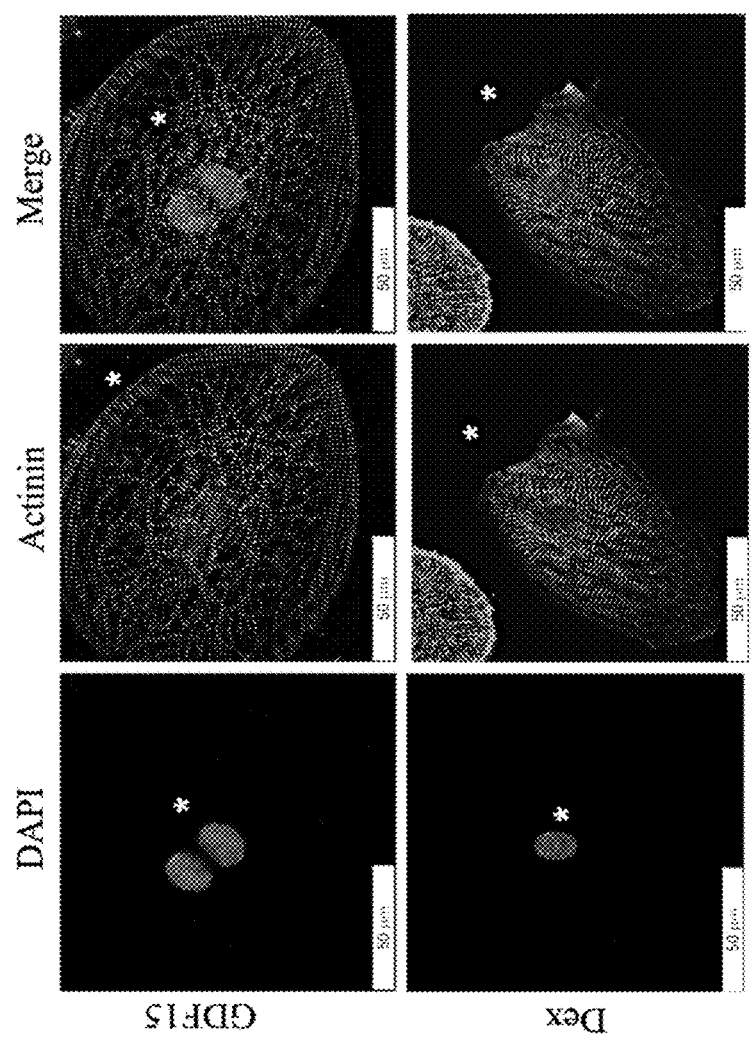
Figure 5J:
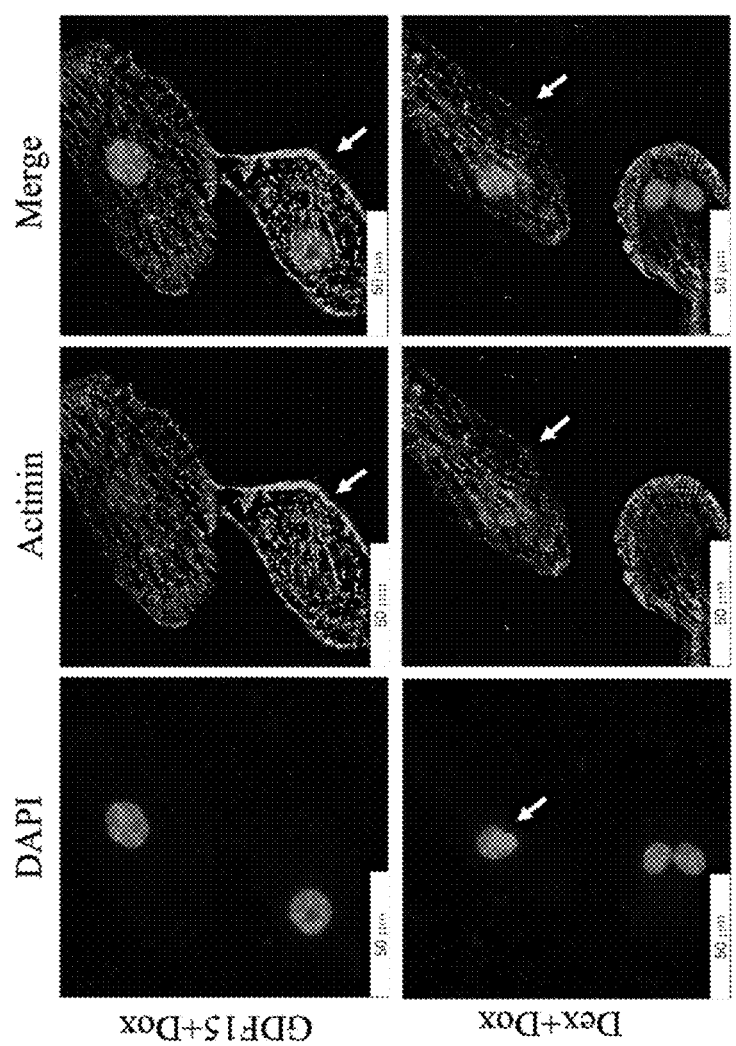
Figures 6E, 6F:
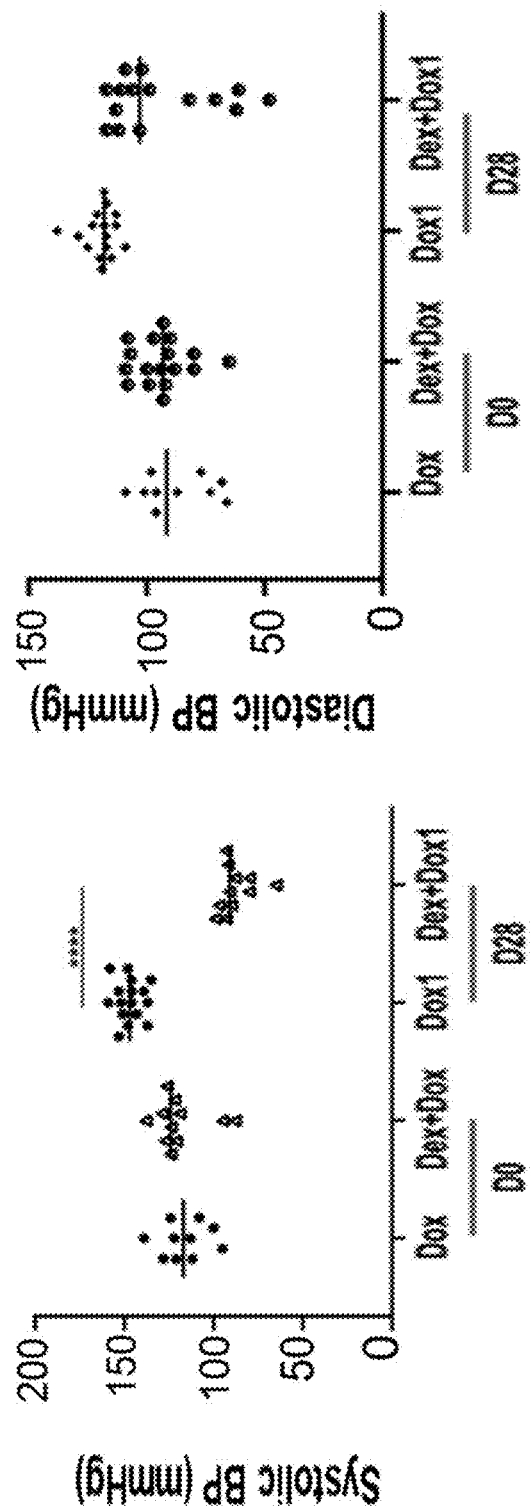

To visualize disruption of the contractile apparatus of hESC-CMs following treatment with doxorubicin, and to observe the protective effects of GDF15 or dexrazoxane in maintaining sarcomeric integrity, immunostaining for a-actinin (FIG. 5H-J) was performed. Whereas untreated hESC-CMs (negative control, CTL) had well-organized, striated sarcomeres similar to GDF15 or Dex only treatment groups, exposure of cells to Dox alone led to considerable disruption of sarcomere structure and nuclear condensation. With GDF15 or dexrazoxane (Dex) pretreatment preceding doxorubicin (Dox), sarcomeric damage was evidently attenuated.

In summary, the results showed that GDF15 can achieve similar or even surprisingly better efficacy to dexrazoxane in reducing cardiac cytotoxicity.

Figure 8A:
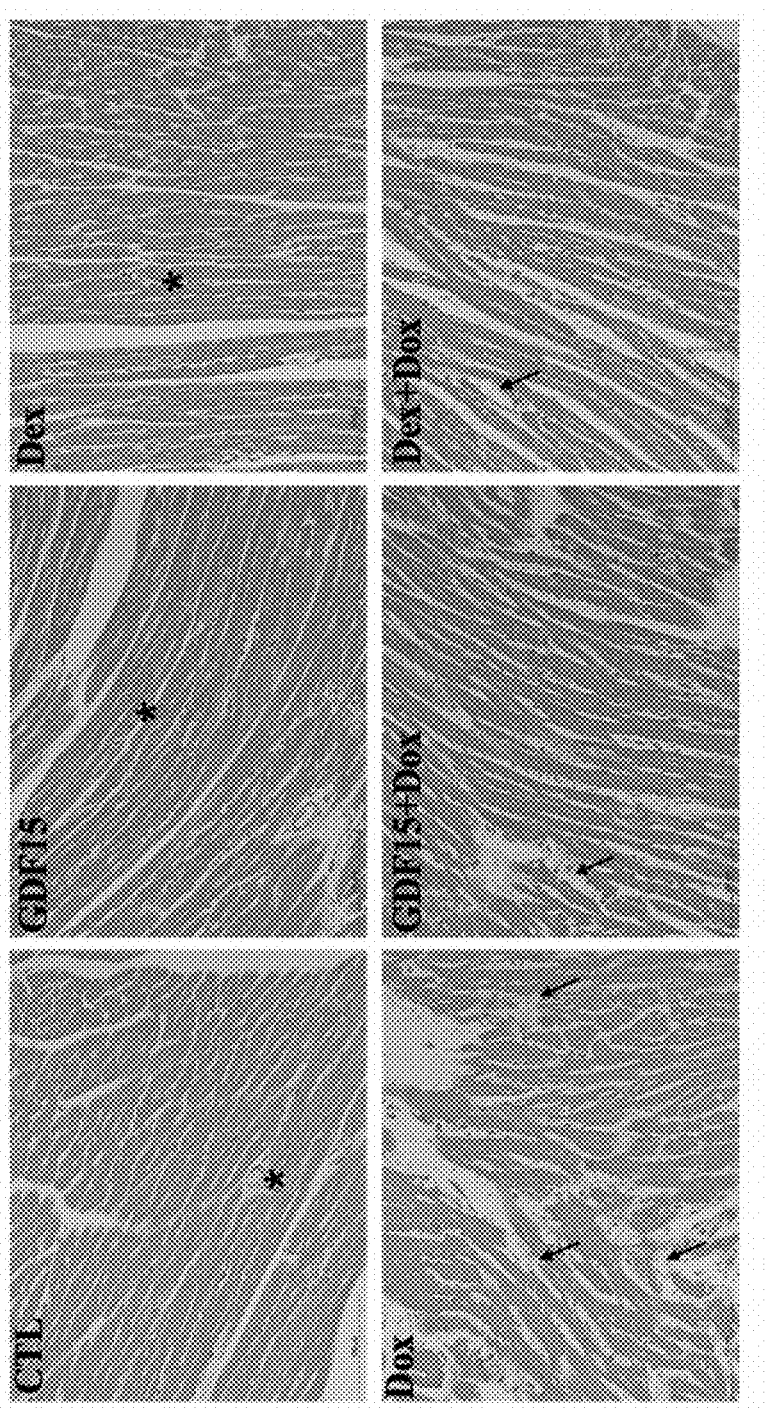
FIG. 8A is the histopathological images of mouse myocardium from mice receiving GDF15 or Dex pretreatment based on hematoxylin and eosin staining, according to an example embodiment.
Figure 8B:
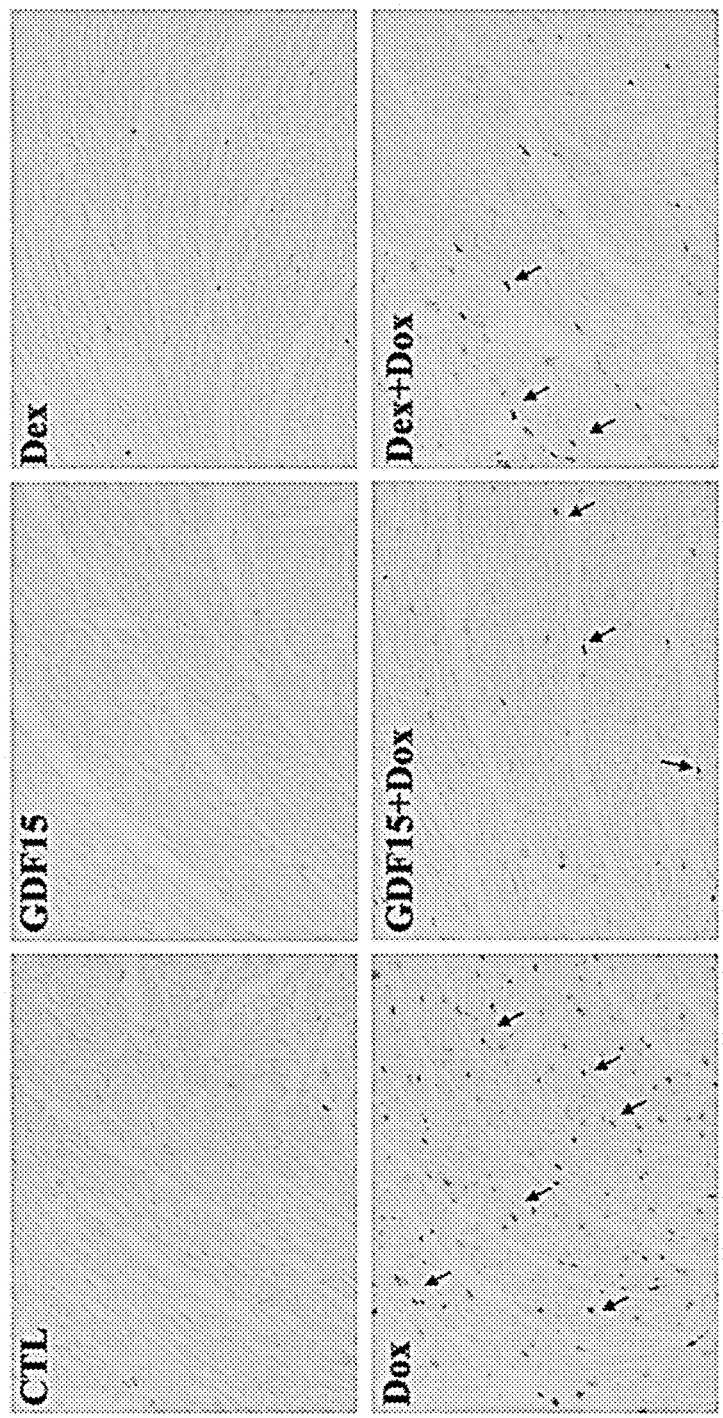
FIG. 8B is the histopathological images of mouse myocardium from mice receiving GDF15 or Dex pretreatment based on TUNEL staining, according to an example embodiment.

5.5 Hypertension and Vascular Dysfunction Secondary to Anthracycline Cardiotoxicity and Nephrotoxicity are Reduced by GDF15 Pretreatment Patients receiving anthracycline often develop hypertension as a result of cardiotoxic and nephrotoxic effects of the drug. Doxorubicin-inducted hypertension reflects vascular stress, dysfunction, inflammation and injury. Pretreatment of mice with intraperitoneal injection of recombinant GDF15 (5 mg/kg, intraperitoneal; comparable to the dosage administered to human individuals) before exposure to doxorubicin significantly lowered systolic and diastolic blood pressure, compared with control animals without GDF15 pretreatment (doxorubicin only; Table 3 and FIGS. 6A-F). Each group contained 4 mice. Systolic and diastolic BP was measured at least twice in each group. Statistical significance was calculated using one-way ANOVA analysis followed by Dunnett's multiple comparisons test. *p<0.001 and **p<0.0001 when comparing the CTL (A,B) with (C-F) Dox at the same time point.

lin and eosin staining revealed myocardial structural disarray, and microfibrillar disruption and disorganization in mice administered doxorubicin that were similarly improved with GDF15 or dexrazoxane pretreatment (FIG. 8A). Using TUNEL staining, the results showed that GDF15 or dexrazoxane pretreated mice had a reduced extent of cardiomyocyte death by apoptosis (FIG. 8B), indicating that myocardial tissue loss, cardiomyocyte death and apoptosis in response to anthracycline was attenuated by GDF15 to a similar extent as for dexrazoxane.

5.7 Cardiac Fibrosis in Response to Anthracycline is Attenuated by GDF15 to a Similar Extent as for Dexrazoxane.

Figure 8C:
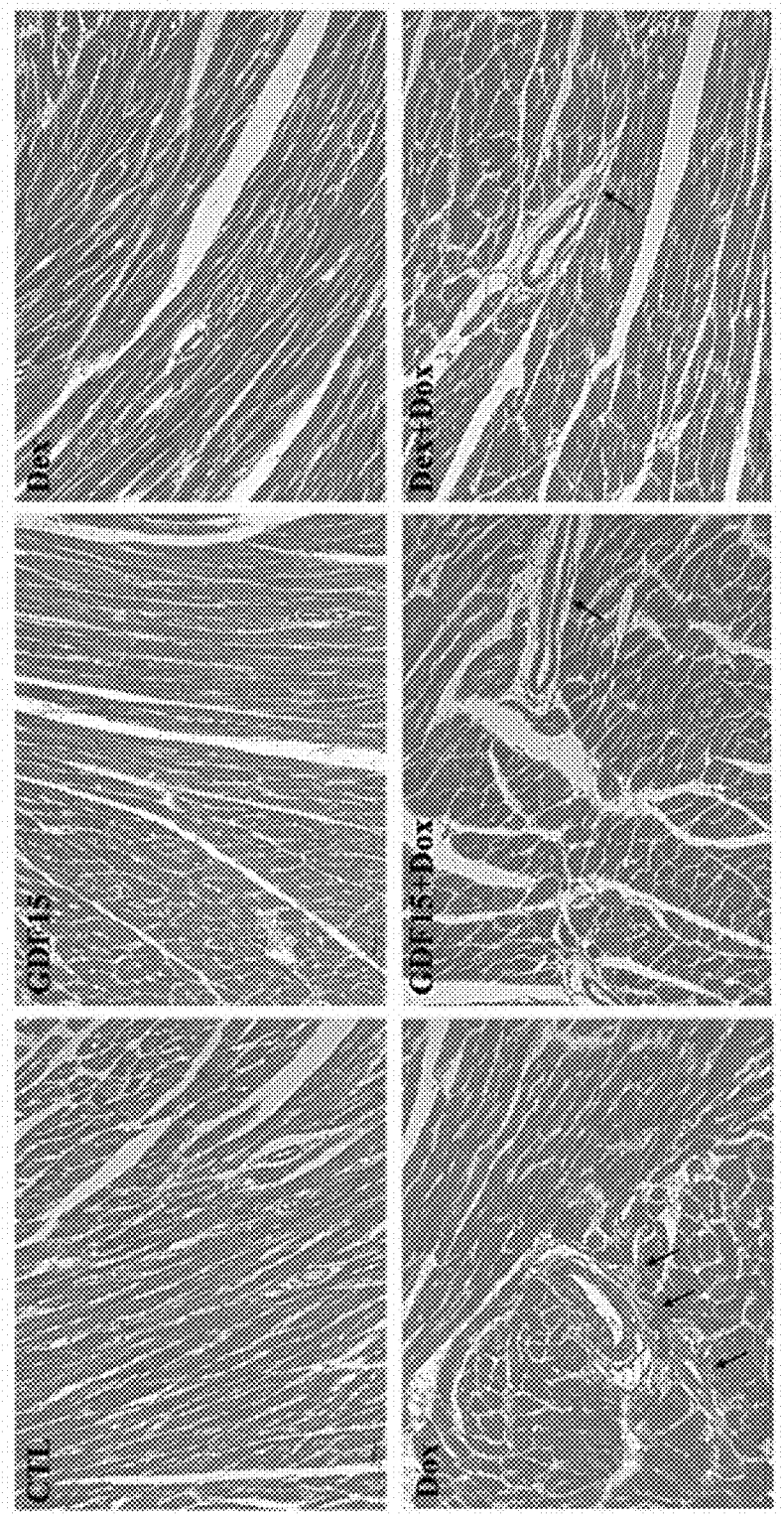
FIG. 8C are histopathological images of mouse myocardium from mice receiving GDF15 or Dex pretreatment based on Masson's trichrome staining, according to an example embodiment.
Figure 8D:
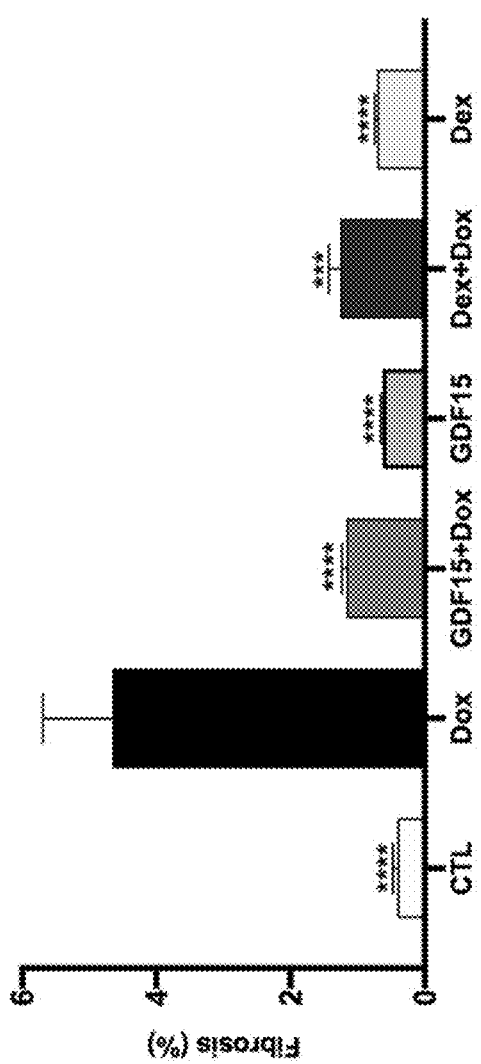
FIG. 8D is a graphical illustration of the extent of cardiac fibrosis in mice receiving GDF15 or Dex pretreatment, according to an example embodiment.

Cardiac fibrosis is an indication of tissue repair following inflammation and damage, and represents non-functioning tissue in terms of myocardial contraction. In previous mouse studies that used a similar doxorubicin cardiotoxicity regimen as for the experiments described herein, it has been shown that cardiac function indicated by ejection fraction was reduced. Moreover, cardiac fibrosis can lead to aberrant cardiac conduction that may arise from fibrotic scar, also known as substrates, that can potentially cause arrhythmias. Cardiac fibrosis in response to anthracycline was attenuated by GDF15 to a similar extent as for dexrazoxane. Using Masson's trichrome staining, the results showed that there was diffuse myocardial interstitial fibrosis as well as perivascular fibrosis in the doxorubicin only group that were visually and quantitatively reduced by GDF15 or dexrazoxane pretreatment (FIG. 8C and 8D).

The data demonstrate that GDF15 is surprisingly effective at reducings the negative impact of anthracycline cardiotoxicity and its associated harmful complications including hypertension, vascular dysfunction, mitochondrial damage, myocardial injury, cardiac fibrosis and cardiac dysfunction. In some embodiments, administering recombinant GDF15 protein at a dose of 300 ng/ml to 1000 ng/ml (1 ug/ml) approximately 24 hours prior to doxorubicin exposure is surprisingly effective at providing very high levels of cardioprotection from doxorubicin, and attenuating hypertension, mitochondrial stress and damage, cardiac fibrosis, and

TABLE 3

Blood pressure measurements before (Day 0) and after (Day 28) doxorubicin administration at 5 mg/kg, intraperitoneal, once weekly for four weeks.

| Group | Pretreatment | Dox | Day 0 SBP (mmHg) | Day 0 DBP (mmHg) | Day 28 SBP (mmHg) | Day 28 DBP (mmHg) |
|---|---|---|---|---|---|---|
| Control | − | − | 112 ± 30 | 76 ± 32 | 107 ± 18 | 87 ± 18 |
| Dox | − | + | 116 ± 13 | 87 ± 15 | 146 ± 7 | 119 ± 7 |
| GDF15 | + | − | 117 ± 12 | 83 ± 17 | 121 ± 5 | 88 ± 5 |
| GDF15 + Dox | + | + | 108 ± 27 | 76 ± 25 | 111 ± 15 | 85 ± 13 |
| Dex | + | − | 114 ± 14 | 78 ± 26 | 108 ± 13 | 84 ± 15 |
| Dex + Dox | + | + | 119 ± 15 | 88 ± 10 | 123 ± 17 | 94 ± 23 |

DBP, diastolic blood pressure; Dex, dexrazoxane; Dox, doxorubicin; GDF15, growth differentiation factor 15; SBP, systolic blood pressure. Four mice (n = 4 independent experiments) in each group.

The results showed that both systolic and diastolic blood pressures of GDF15+Dox treatment group were lower than that of Dex+Dox treatment group, indicating that hypertension and vascular dysfunction secondary to anthracycline cardiotoxicity and nephrotoxicity were reduced by GDF15 pretreatment.

Figure 7:
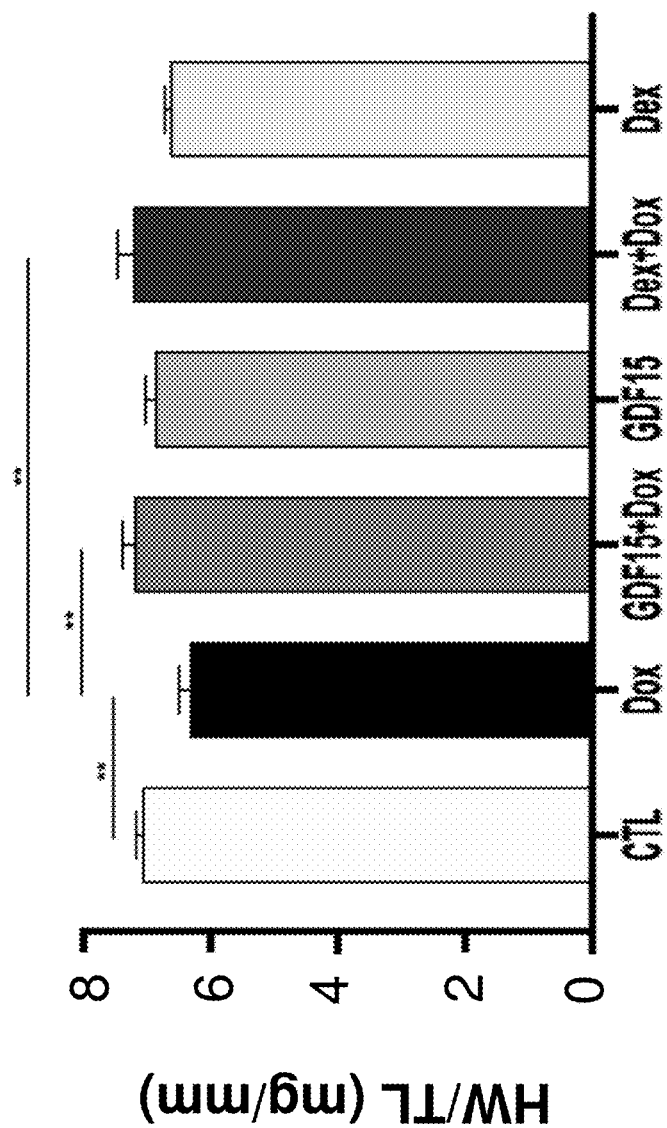
FIG. 7 is a graphical illustration of heart weight-to-tibial length (HW/TL) ratio of the heart tissue of mice upon pretreatment of GDF15 or Dex, in the presence of Dox, according to an example embodiment.

5.6 Myocardial Tissue Loss, Cardiomyocyte Death and Apoptosis in Response to Anthracycline was Attenuated by GDF15 to a Similar Extent as for Dexrazoxane Myocardial tissue loss following doxorubicin exposure was indicated by a decrease in the heart weight-to-tibia length ratio (FIG. 7). Histopathologic analysis by hematoxycardiomyocyte apoptosis to an extent that is surprisingly comparable to that of dexrazoxane.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein. For example, recombinant GDF-15 protein (PeproTech, Inc.) was used for certain example compositions, but other GDF-15 protein, or a functional variant or homolog thereof may be used.

What is claimed is:

1. A method of treating or preventing a disease, condition or disorder resulting from or exacerbated by chemotherapy treatment in a subject, comprising the step of:
   administering an effective amount of GDF15 to the subject receiving the chemotherapy treatment such that the disease, condition or disorder is improved;
   wherein the chemotherapy treatment comprises at least one round of anthracycline administration; and
   wherein the disease, condition or disorder is selected from the group consisting of cardiotoxicity, cardiac dysfunction, hypertension, vascular dysfunction, mitochondrial damage, mitochondrial dysfunction, sarcomere disruption, myocardial injury, myocardial tissue loss, cardiac fibrosis, cardiomyocyte apoptosis, and cardiomyocyte death.

2. The method of claim 1, wherein the step of administering an effective amount of GDF15 to the subject is performed prior to the anthracycline administration.

3. The method of claim 1, wherein the step of administering an effective amount of GDF15 to the subject is performed prior to each round of anthracycline administration.

4. The method of claim 3, wherein the anthracycline is selected from the group consisting of doxorubicin, epirubicin, daunorubicin, and idarubicin.

5. The method of claim 1, wherein the GDF15 is a recombinant human GDF15.

6. The method of claim 1, wherein the GDF15 comprises an amino acid sequence SEQ ID NO: 1, or a functional variant or homolog thereof.

7. The method of claim 3, wherein the anthracycline is doxorubicin.

8. The method of claim 3, wherein the anthracycline is daunorubicin.

* * * * *